United States Patent
Asfora

(10) Patent No.: US 10,004,507 B2
(45) Date of Patent: Jun. 26, 2018

(54) VASCULAR ANASTOMOSIS DEVICE AND METHOD

(71) Applicant: Asfora IP, LLC, Sioux Falls, SD (US)

(72) Inventor: Wilson Theophilo Asfora, Sioux Falls, SD (US)

(73) Assignee: ASFORA IP, LLC, Sioux Falls, SD (US)

( * ) Notice: Subject to any disclaimer, the term of this patent is extended or adjusted under 35 U.S.C. 154(b) by 0 days. days.

(21) Appl. No.: 13/725,936

(22) Filed: Dec. 21, 2012

(65) Prior Publication Data

US 2014/0180315 A1 Jun. 26, 2014
US 2017/0143343 A9 May 25, 2017

Related U.S. Application Data

(62) Division of application No. 11/820,053, filed on Jun. 18, 2007, now Pat. No. 8,361,092.

(51) Int. Cl.
*A61B 17/11* (2006.01)
*A61B 17/06* (2006.01)

(52) U.S. Cl.
CPC ........ *A61B 17/11* (2013.01); *A61B 17/06166* (2013.01); *A61B 2017/1107* (2013.01); *A61B 2017/1135* (2013.01)

(58) Field of Classification Search
CPC . A61B 17/08; A61B 17/11; A61B 2017/1107; A61B 2017/1132; A61B 2017/1135; A61B 2017/1139; A61B 17/06166

USPC ............... 606/151, 152, 153, 154, 155, 156; 623/1.23, 1.36
See application file for complete search history.

(56) References Cited

U.S. PATENT DOCUMENTS

| | | | |
|---|---|---|---|
| 4,368,736 A | | 1/1983 | Kaster |
| 4,503,568 A | | 3/1985 | Madras |
| 4,657,019 A | | 4/1987 | Walsh et al. |
| 4,771,775 A | | 9/1988 | Walsh et al. |
| 4,787,386 A | * | 11/1988 | Walsh et al. ............. 606/153 |
| 4,873,975 A | * | 10/1989 | Walsh et al. ............. 606/153 |
| 4,917,087 A | | 4/1990 | Walsh et al. |
| 4,917,091 A | | 4/1990 | Berggren et al. |
| 5,643,340 A | | 7/1997 | Nunokawa |
| 5,695,504 A | | 12/1997 | Gifford, III et al. |
| 5,702,048 A | | 12/1997 | Eberlin |
| 5,725,544 A | | 3/1998 | Rygaard |
| 5,732,872 A | | 3/1998 | Bolduc et al. |
| 5,755,778 A | | 5/1998 | Kleshinski |
| 5,779,718 A | | 7/1998 | Green et al. |
| 5,799,857 A | | 9/1998 | Robertson et al. |
| 5,800,522 A | | 9/1998 | Campbell et al. |
| 5,817,113 A | | 10/1998 | Gifford, III et al. |
| 5,833,698 A | | 11/1998 | Hinchliffe et al. |
| 5,843,127 A | | 12/1998 | Li |
| 5,868,763 A | | 2/1999 | Spence et al. |
| 5,879,371 A | | 3/1999 | Gardiner et al. |
| 5,881,943 A | | 3/1999 | Heck et al. |

(Continued)

*Primary Examiner* — Ryan J Severson
*Assistant Examiner* — Christian Knauss
(74) *Attorney, Agent, or Firm* — Dorsey & Whitney LLP

(57) ABSTRACT

A side-to-end vascular anastomosis device comprising a diversion conduit coupled to a lower flange which is inserted into the vessel and an upper flange located on the outside of the vessel designed to clamp together to seal the incision into which the lower flange of the device is inserted.

13 Claims, 22 Drawing Sheets

(56) References Cited

U.S. PATENT DOCUMENTS

| | | | | |
|---|---|---|---|---|
| 5,893,369 A | * | 4/1999 | LeMole | 606/184 |
| 5,904,697 A | | 5/1999 | Gifford, III et al. | |
| 5,915,616 A | | 6/1999 | Viola et al. | |
| 5,921,995 A | | 7/1999 | Kleshinski | |
| 5,944,730 A | | 8/1999 | Nobles et al. | |
| 5,947,363 A | | 9/1999 | Bolduc et al. | |
| 5,957,363 A | | 9/1999 | Heck | |
| 5,968,089 A | * | 10/1999 | Krajicek | 623/1.15 |
| 5,972,017 A | | 10/1999 | Berg et al. | |
| 5,976,159 A | | 11/1999 | Bolduc et al. | |
| 6,001,124 A | | 12/1999 | Bachinski | |
| 6,007,544 A | | 12/1999 | Kim | |
| 6,007,576 A | * | 12/1999 | McClellan | 623/23.64 |
| 6,015,416 A | | 1/2000 | Stefanchik et al. | |
| 6,024,748 A | | 2/2000 | Manzo et al. | |
| 6,030,370 A | | 2/2000 | Kupka et al. | |
| 6,036,699 A | | 3/2000 | Andreas et al. | |
| 6,036,700 A | | 3/2000 | Stefanchik et al. | |
| 6,036,702 A | | 3/2000 | Bachinski et al. | |
| 6,036,703 A | | 3/2000 | Evans et al. | |
| 6,036,704 A | | 3/2000 | Yoon | |
| 6,036,705 A | | 3/2000 | Nash et al. | |
| 6,050,472 A | | 4/2000 | Shibata | |
| 6,056,762 A | | 5/2000 | Nash et al. | |
| 6,066,148 A | | 5/2000 | Rygaard | |
| 6,068,637 A | | 5/2000 | Popov et al. | |
| 6,074,416 A | | 6/2000 | Berg et al. | |
| 6,110,188 A | | 8/2000 | Narciso, Jr. | |
| 6,113,612 A | | 9/2000 | Swanson et al. | |
| 6,120,432 A | | 9/2000 | Sullivan et al. | |
| 6,146,393 A | | 11/2000 | Wakabayashi | |
| 6,149,681 A | | 11/2000 | Houser et al. | |
| 6,152,937 A | | 11/2000 | Peterson et al. | |
| 6,165,185 A | | 12/2000 | Shennib et al. | |
| 6,171,319 B1 | | 1/2001 | Nobles et al. | |
| 6,176,413 B1 | | 1/2001 | Heck et al. | |
| 6,176,864 B1 | | 1/2001 | Chapman et al. | |
| 6,186,942 B1 | | 2/2001 | Sullivan et al. | |
| 6,187,019 B1 | | 2/2001 | Stefanchik et al. | |
| 6,187,020 B1 | | 2/2001 | Zegdi et al. | |
| 6,190,397 B1 | | 2/2001 | Spence et al. | |
| 6,190,590 B1 | | 2/2001 | Randall et al. | |
| 6,193,129 B1 | | 2/2001 | Bittner et al. | |
| 6,193,734 B1 | | 2/2001 | Bolduc et al. | |
| 6,206,912 B1 | | 3/2001 | Goldsteen et al. | |
| 6,235,054 B1 | | 5/2001 | Berg et al. | |
| 6,245,083 B1 | | 6/2001 | Black et al. | |
| 6,248,117 B1 | | 6/2001 | Blatter et al. | |
| 6,280,460 B1 | | 8/2001 | Bolduc et al. | |
| 6,293,965 B1 | | 9/2001 | Berg et al. | |
| 6,309,416 B1 | | 10/2001 | Swanson et al. | |
| 6,371,965 B2 | | 4/2002 | Gifford, III et al. | |
| 6,395,015 B1 | * | 5/2002 | Borst et al. | 606/213 |
| 6,402,767 B1 | * | 6/2002 | Nash et al. | 606/153 |
| 6,443,965 B1 | | 9/2002 | Gifford, III et al. | |
| 6,450,390 B2 | | 9/2002 | Heck et al. | |
| 6,451,034 B1 | | 9/2002 | Gifford, III et al. | |
| 6,451,048 B1 | | 9/2002 | Berg et al. | |
| 6,461,320 B1 | | 10/2002 | Yencho et al. | |
| 6,485,496 B1 | | 11/2002 | Suyker et al. | |
| 6,488,692 B1 | * | 12/2002 | Spence et al. | 606/153 |
| 6,491,704 B2 | | 12/2002 | Gifford, III et al. | |
| 6,497,710 B2 | * | 12/2002 | Yencho et al. | 606/153 |
| 6,517,558 B2 | | 2/2003 | Gittings et al. | |
| 6,524,322 B1 | * | 2/2003 | Berreklouw | 606/153 |
| 6,533,812 B2 | | 3/2003 | Swanson et al. | |
| 6,537,287 B1 | | 3/2003 | Yencho et al. | |
| 6,551,334 B2 | | 4/2003 | Blatter et al. | |
| 6,569,173 B1 | | 5/2003 | Blatter et al. | |
| 6,589,277 B1 | * | 7/2003 | Fabiani et al. | 623/1.31 |
| 6,599,303 B1 | | 7/2003 | Peterson et al. | |
| 6,620,176 B1 | | 9/2003 | Peterson | |
| 6,623,494 B1 | | 9/2003 | Blatter | |
| 6,652,542 B2 | | 11/2003 | Blatter et al. | |
| 6,659,327 B2 | | 12/2003 | Heck et al. | |
| 6,673,084 B1 | | 1/2004 | Peterson et al. | |
| 6,676,678 B2 | | 1/2004 | Gifford, III et al. | |
| 6,685,726 B2 | | 2/2004 | Black et al. | |
| 6,709,441 B2 | | 3/2004 | Bolduc et al. | |
| 6,726,694 B2 | | 4/2004 | Blatter et al. | |
| 6,726,923 B2 | | 4/2004 | Iyer et al. | |
| 6,740,101 B2 | | 5/2004 | Houser et al. | |
| 6,743,244 B2 | | 6/2004 | Blatter et al. | |
| 6,805,708 B1 | | 10/2004 | Yencho et al. | |
| 6,843,795 B1 | | 1/2005 | Houser et al. | |
| 6,899,718 B2 | | 5/2005 | Gifford, III et al. | |
| 6,962,596 B2 | | 11/2005 | Bolduc et al. | |
| 6,966,917 B1 | | 11/2005 | Suyker et al. | |
| 7,018,387 B2 | | 3/2006 | Suyker et al. | |
| 7,029,481 B1 | * | 4/2006 | Burdulis et al. | 606/148 |
| 7,108,702 B2 | | 9/2006 | Yencho et al. | |
| 7,112,211 B2 | | 9/2006 | Gifford, III et al. | |
| 7,112,212 B2 | | 9/2006 | Raza | |
| 7,160,311 B2 | | 1/2007 | Blatter et al. | |
| 7,182,771 B1 | | 2/2007 | Houser et al. | |
| 7,371,243 B1 | * | 5/2008 | Nielsen et al. | 606/142 |
| 7,708,769 B1 | * | 5/2010 | Manzo et al. | 623/1.1 |
| 8,361,092 B1 | * | 1/2013 | Asfora | 606/153 |
| 9,504,469 B2 | | 11/2016 | Asfora | |
| 2001/0041902 A1 | * | 11/2001 | Lepulu | A61B 17/11 606/153 |
| 2001/0044631 A1 | | 11/2001 | Akin et al. | |
| 2002/0143347 A1 | * | 10/2002 | Cole et al. | 606/153 |
| 2003/0028205 A1 | * | 2/2003 | Vargas et al. | 606/153 |
| 2003/0065344 A1 | * | 4/2003 | Kirsch et al. | 606/153 |
| 2003/0225425 A1 | * | 12/2003 | Kupiecki et al. | 606/153 |
| 2004/0220597 A1 | * | 11/2004 | Willis et al. | 606/153 |
| 2005/0165428 A1 | * | 7/2005 | Franco | 606/153 |
| 2005/0192604 A1 | * | 9/2005 | Carson et al. | 606/153 |
| 2005/0251155 A1 | | 11/2005 | Orban, III et al. | |
| 2005/0251163 A1 | * | 11/2005 | Tilson et al. | 606/153 |
| 2006/0100648 A1 | * | 5/2006 | Roy et al. | 606/153 |
| 2006/0167476 A1 | * | 7/2006 | Burdulis et al. | 606/144 |
| 2006/0282106 A1 | | 12/2006 | Cole et al. | |

* cited by examiner

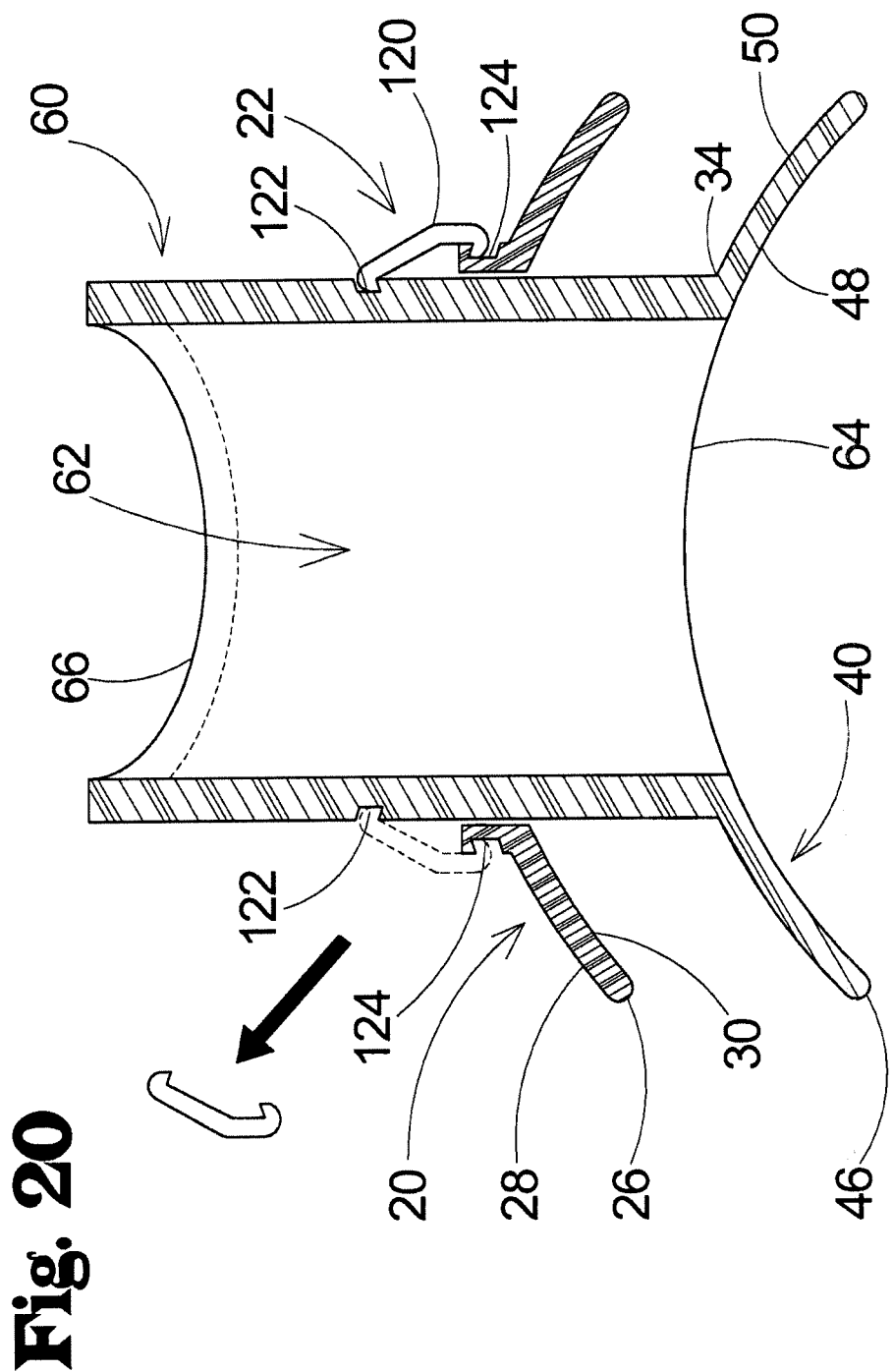

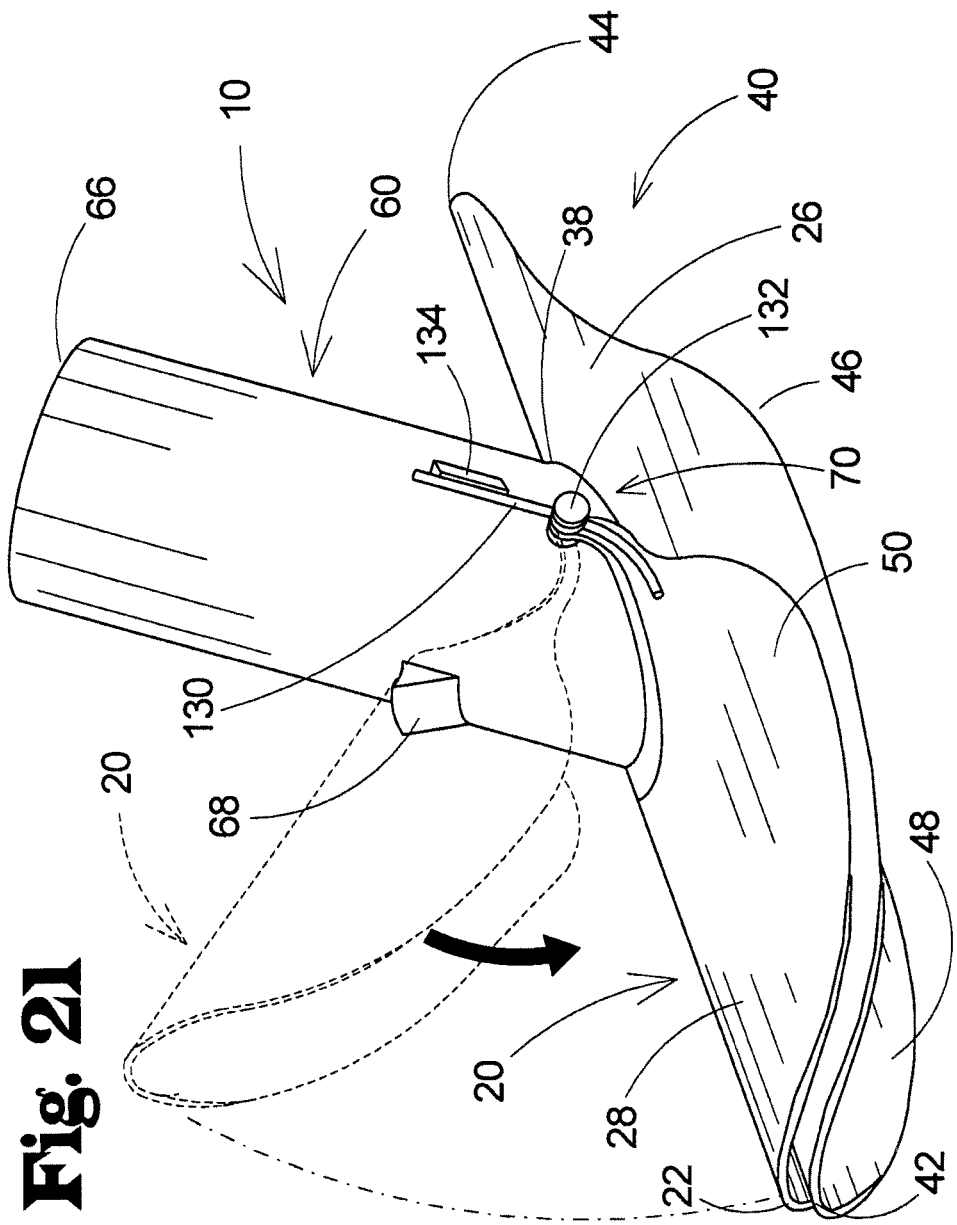

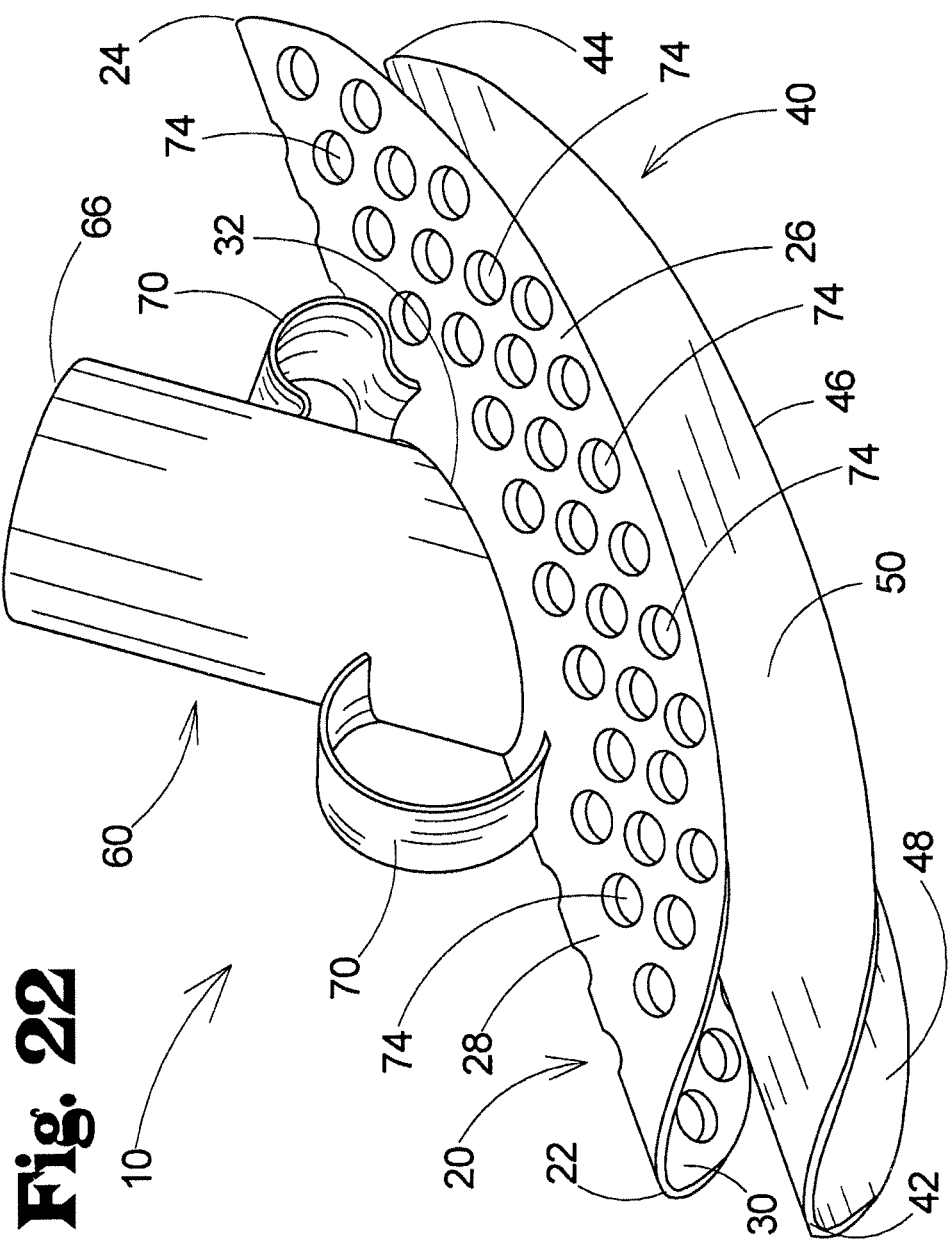

VASCULAR ANASTOMOSIS DEVICE AND METHOD

CROSS-REFERENCE TO RELATED APPLICATIONS

This application is a divisional of U.S. patent application Ser. No. 11/820,053, filed Jun. 18, 2007, now U.S. Pat. No. 8,361,092, issued Jan. 29, 2013, which is incorporated by reference herein in its entirety for all purposes.

FIELD

The present disclosure relates to devices and methods for performing a side-to-end vascular anastomosis.

BACKGROUND

A side-to-end vascular anastomosis, in which an end of a vessel is surgically joined to the side of another vessel within a patient, is required for a variety of medical procedures. For example; a cranial bypass utilizes the flow of the temporal artery located on the outside of the skull to divert a portion of its flow to one of the arteries within the skull to provide additional blood flow within the patient's brain. One of the major considerations when performing any anastomosis is that the flow of bodily fluid within the vessel must be interrupted for the duration of the procedure of joining the vessels. This interruption of flow may have a detrimental effect on the proximal tissue and to the patient's health in general.

The most common method of vascular anastomosis that is presently practiced is hand suturing one vessel to the other. This process is not only difficult and time consuming, but requires a high degree of surgical skill and a considerable amount of time and patience, as a plurality of sutures are required to achieve a fluid impermeable seal between the two vessels. Incorrect suturing requires additional sutures, and in turn increases the time which the flow of bodily fluid must remain suspended.

Therefore, in view of the foregoing, what is needed in the art is a more rapid and dependable system of vascular side-to-end anastomosis which would require less time to reliably join the vessels and therefore decrease the duration of suspended flow and as a result pose less of a health threat to the patient.

SUMMARY

To meet these needs, the embodiments and implementations of the present invention provide a device as a well as a technique that permits the rapid installation of a reliable side-to-end anastomotic diversion so that the duration of suspended flow can be reduced to a fraction of the time required for the presently practiced method.

One aspect of the invention comprises a vascular anastomosis device that includes a lower flange having an interior surface and a lower gripping surface and a diversion conduit attached to the lower flange, with the diversion conduit having an inlet, an outlet, and a lumen extending between the inlet and outlet. The device further includes an upper flange capable of moving from a first position to a second position with respect to the lower flange. The second position of the upper flange is characterized by the upper flange being closer to the lower flange than when the upper flange is in the first position. The upper flange has an exterior surface and an upper gripping surface. The device also includes a biasing structure configured to bias the upper flange from the first position toward the second position.

In another aspect of the invention, a method of installing a vascular anastomosis device in a vascular conduit includes clamping off flow through a portion of the vascular conduit, creating an incision in the vascular conduit for insertion of the vascular anastomosis device, inserting a lower flange of the vascular anastomosis device through the incision and into the vascular conduit, and clamping the vascular anastomosis device on the vascular conduit.

In yet another aspect of the invention, a vascular anastomosis device includes a lower flange for insertion into a first vascular conduit, with the lower flange having a gripping surface for holding in place interior vascular tissue of the first vascular conduit. A diversion conduit is mounted on the lower flange for redirecting a portion of vascular contents of the first vascular conduit to a second vascular conduit. The diversion conduit comprises a conduit orifice allowing a portion of the vascular contents to divert, a conduit outlet for attachment to a second vascular conduit of the anastomosis, and a lumen for conducting bodily fluid from the conduit orifice to the outlet. The device may further include an upper flange configured to fit over a portion of the first vascular conduit, the upper flange having a gripping surface for holding in place exterior vascular tissue of the first vascular conduit, with the gripping surface of the upper flange being configured in opposition to the gripping surface of the lower flange. The device may also include a biasing structure configured to apply force to the upper flange to move the upper flange toward the lower flange.

In still yet another aspect, the invention includes a vascular anastomosis device that comprises a lower flange having a diversion conduit with an inlet and an outlet, and an upper flange movable on the diversion conduit between a first position separated from the lower flange and a second position closer to the lower flange.

In another aspect, the invention includes a method of installing a vascular anastomosis device that comprises making an incision in a vascular conduit, inserting a lower flange of the device through the incision such that an upper flange, in a position separated from the lower flange, is positioned external to the incision, and moving the upper flange from its separated position to a second position to clamp the vascular conduit between the upper and lower flanges.

Further advantages of the embodiments, along with the various features of novelty, are pointed out with particularity in the claims annexed to and forming a part of this disclosure. For a better understanding of the disclosure, reference is made to the accompanying drawings and descriptive matter in which there are illustrated various embodiments of the invention.

DESCRIPTION OF THE DRAWINGS

FIG. 20 is a cross-sectional view of a vascular anastomosis device demonstrating a removable retention device in accordance with still another embodiment of the present invention.

FIG. 21 is a schematic perspective view of a vascular anastomosis device embodiment demonstrating an alternately designed upper flange that employs a hinge spring biasing element.

FIG. 22 is a schematic perspective view of a vascular anastomosis device demonstrating a perforated upper flange embodiment of the present invention.

DETAILED DESCRIPTION

In the following detailed description, reference is made to the accompanying drawings which form a part hereof, and in which is shown by way of illustration specific embodiments in which the invention may be practiced. These embodiments are described in detail sufficient to enable those skilled in the art to practice the invention, and it is to be understood that other embodiments may be utilized and that structural, logical and mechanical changes may be made without departing from the scope of the present invention. The following detailed description is, therefore, not to be taken in a limiting sense, and the scope of the present invention is defined by the appended claims.

Figure 1:
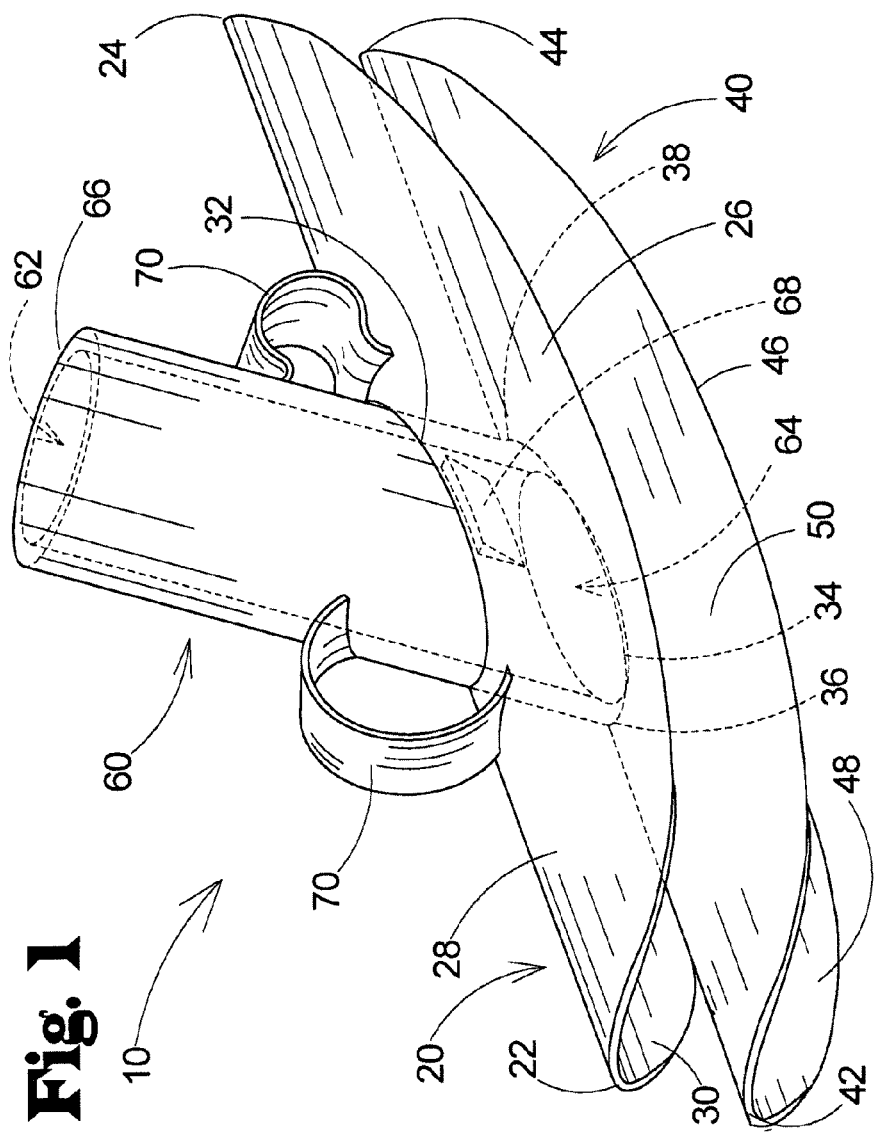
FIG. 1 is a schematic perspective view of a vascular anastomosis device in an open configuration in accordance with one embodiment of the present invention.

One embodiment of a vascular anastomosis device (10) is shown in FIG. 1 and in more detail in FIGS. 2 through 6. The structure of the vascular anastomosis device (10) may have three major substructures including an upper flange (20), a lower flange (40) and a diversion conduit (60). The lower flange (40) and the diversion conduit (60) may be formed from a single piece of material or may be formed of separate pieces that are permanently fixed or joined to one another. The combination of the lower flange (40) and the diversion conduit (60) may be characterized as the static or stationary parts of the vascular anastomosis device (10), while the upper flange (20) may be movable with respect to the lower flange (40) between a first or open position and a second or closed position.

Figure 7:
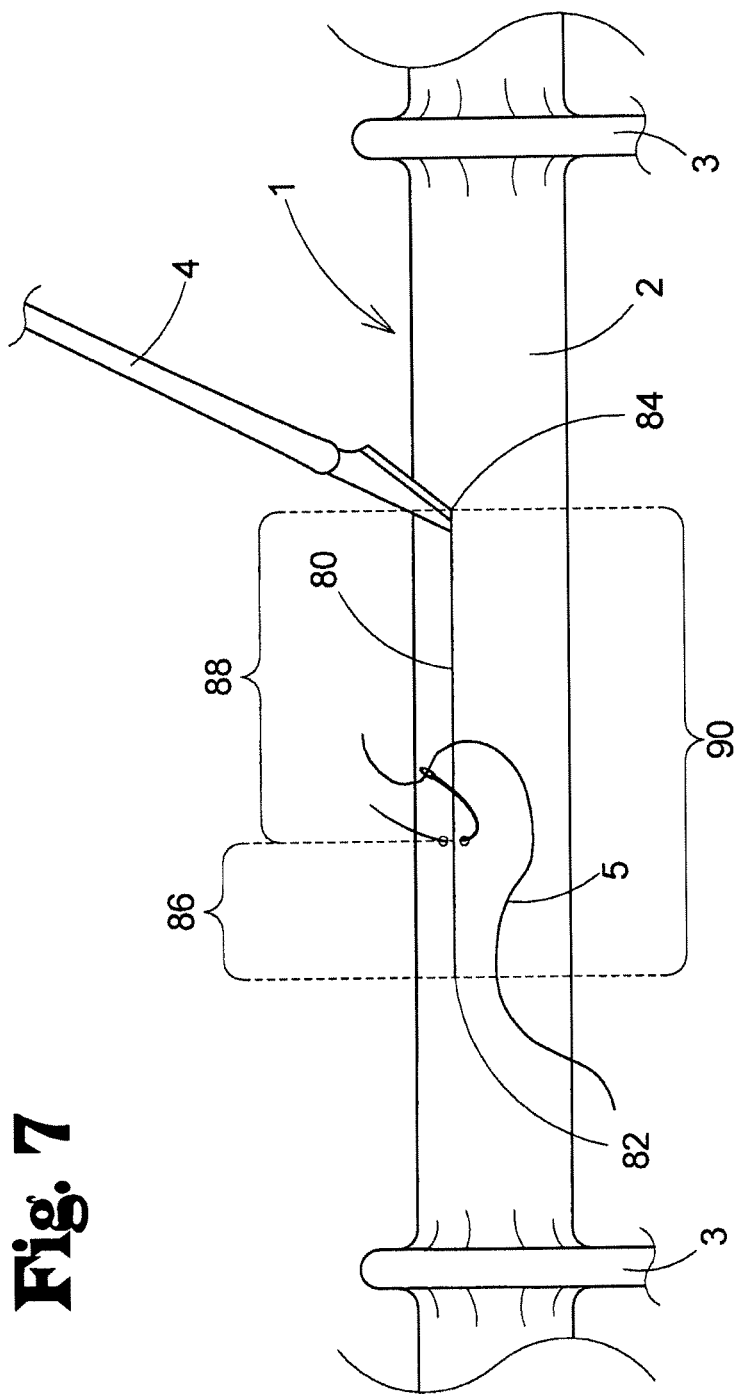
FIG. 7 is a schematic view of a vascular conduit which is being incised and having a suture set in preparation to accept a vascular anastomosis device, in accordance with another embodiment of the present invention.

The upper (20) and lower (40) flanges may be formed with a curvature that is generally complementary to the circumference of the first vascular conduit (1) (as shown in FIG. 7) to which they will be attached, with the curvature of the lower gripping surface (50) of the lower flange (40) conforming generally to the interior circumference of the first vascular conduit (1) and the upper gripping surface (30) of the upper flange (20) generally conforming to the exterior circumference of the first vascular conduit (1).

In some embodiments, the upper flange (20) includes an upper anterior end (22) which may be oriented in an upstream direction on the exterior of the first vascular conduit (1). Similarly, the upper flange (20) includes an upper posterior end (24) which may be oriented in a downstream direction on the exterior of the first vascular conduit (1). A line extending between the upper anterior end (22) and the upper posterior end (24) runs generally parallel to the flow of fluid through the first vascular conduit (1). The upper perimeter (26) extends along the edge of the upper flange (20) and runs from the upper anterior end (22) to the upper posterior end (24) on both sides of the upper flange (20). When applied to the body of a patient, the exterior surface (28) of the upper flange (20) is positioned adjacent to the surrounding bodily tissue, and the upper gripping surface (30) is in contact with the exterior vascular tissue (2) of the first vascular conduit (1).

In such embodiments, the lower flange (40) includes a lower anterior end (42) which may be oriented in an upstream direction within the first vascular conduit (1). Similarly, the lower flange (40) includes a lower posterior end (44) which may be oriented in a downstream direction within the first vascular conduit (1). A line extending between the lower anterior end (42) and the lower posterior end (44) runs generally parallel to the flow of fluid through the first vascular conduit (1). The lower perimeter (46) extends along the edge of the lower flange (40) and runs from the lower anterior end (42) to the lower posterior end (44) on both sides of the lower flange (40). When applied to the body of a patient, the interior surface (48) of the lower flange (40) is positioned adjacent to the contents within the first vascular conduit (1), and the lower gripping surface (50) is in contact with the interior vascular tissue (2) of the first vascular conduit (1).

Optionally, the upper gripping surface (30) of the upper flange (20) and the lower gripping surface (50) of the lower flange (40) may include texturing or contouring that enhances the grip on or engagement with the vascular tissue (2) by the respective flanges. In further embodiments, the respective gripping surfaces may also include a bio-adhesive substance to adhere to or bond with the vascular tissue (2). Such a bio-adhesive may be activated by the moisture present at the anastomosis site. The activation of the bio-adhesive may take a length of time adequate to position and/or set the vascular anastomosis device (10) before adhering to the vascular tissue (2).

The diversion conduit (60) is joined to the lower flange (40). The diversion conduit (60) and the lower gripping surface (50) of the lower flange (40) meet at a seam (34). The seam (34) includes an anterior side of the seam (36) and a posterior side of the seam (38). The diversion conduit (60) includes a lumen (62) that extends from the inlet (64) which forms an opening in the interior surface (48) to the outlet (66) which is intended to be joined to the second vascular conduit (not shown) of the anastomosis. The diversion conduit (60) may be joined to the lower flange (40) at an angle. The angle formed by the lower flange (40) and the diversion conduit (60) is in some embodiments an obtuse angle so as to limit turbulence in the vascular flow as would be beneficial in arterial or veinal vessels but the invention is not so limited as the angle formed by the lower flange (40) and the diversion conduit (60) may be acute, right or obtuse depending on the intended characteristics of the tubular conduit to which the anastomosis. For example; some applications of the invention, such as, for example, the vas deferens or a bile duct or a ureter, require little consideration of turbulence in the vascular flow.

In various embodiments, the upper flange (20) may be connected to the diversion conduit (60) using the biasing structure or element (70) which exerts force on the upper flange (20) to bias the upper flange (20) toward the lower flange (40). The biasing element (70) may comprise a variety of mechanisms that apply a force in both active and passive ways. An active biasing means may be defined as mechanisms that store and exert a force while passive biasing means may be defined as mechanisms that hold or sustain the force applied by a separate or external source. Examples of active means biasing mechanisms may include by way of example only and not limitation; springs, expandable masses, elastic structures, pressure vessels, semi-deformable materials and the like. Examples of passive means biasing mechanisms may include by way of example only and not limitation; wedges, threaded screws, retention pins, locking devices and the like. The biasing element (70) may include a single biasing means of either active or passive type or a combination of means of one or both types. Illustratively, FIGS. 1 through 6 show a pair of deformable leaves or leaf springs mounted on opposite sides of the diversion conduit (60) connecting to the exterior surface (28) of the upper flange (20) that act as the biasing element (70). It should be understood that a wide variety of other mechanisms, known to those skilled in the art, may be employed to bias the upper flange (20) toward the lower flange (40) without deviating from the scope of the invention. The biasing element (70) may exert force on the upper flange (20) to position the upper flange (20) generally closer to or in contact with the lower flange (40). During installation the biasing element (70) may impart force to move the upper flange (20) from a first position further away from the lower flange (40) to a second position relatively closer to the lower flange (40). When in use, the biasing element (70) tends to force the upper flange (20) toward the lower flange (40) to cause the flanges to grip a portion of the first vascular conduit (1) and thus may produce a seal between the vascular anastomosis device (10) and the first vascular conduit (1) to thereby minimize the loss of any vascular material from the first vascular conduit (1).

The upper flange (20) may include in some embodiments an aperture (32) through which the diversion conduit (60) may pass. In the embodiment illustrated in FIGS. 1 through 6, the aperture (32) is configured to allow the upper flange (20) to slide along the length of the diversion conduit (60) substantially from the seam (34) to the points at which the biasing element (70) is attached to the diversion conduit (60). In other embodiments, such as the embodiment depicted in FIG. 21, an aperture (32) may not be included as the upper flange (20) does not move along the length of the diversion conduit (60).

Figure 2:
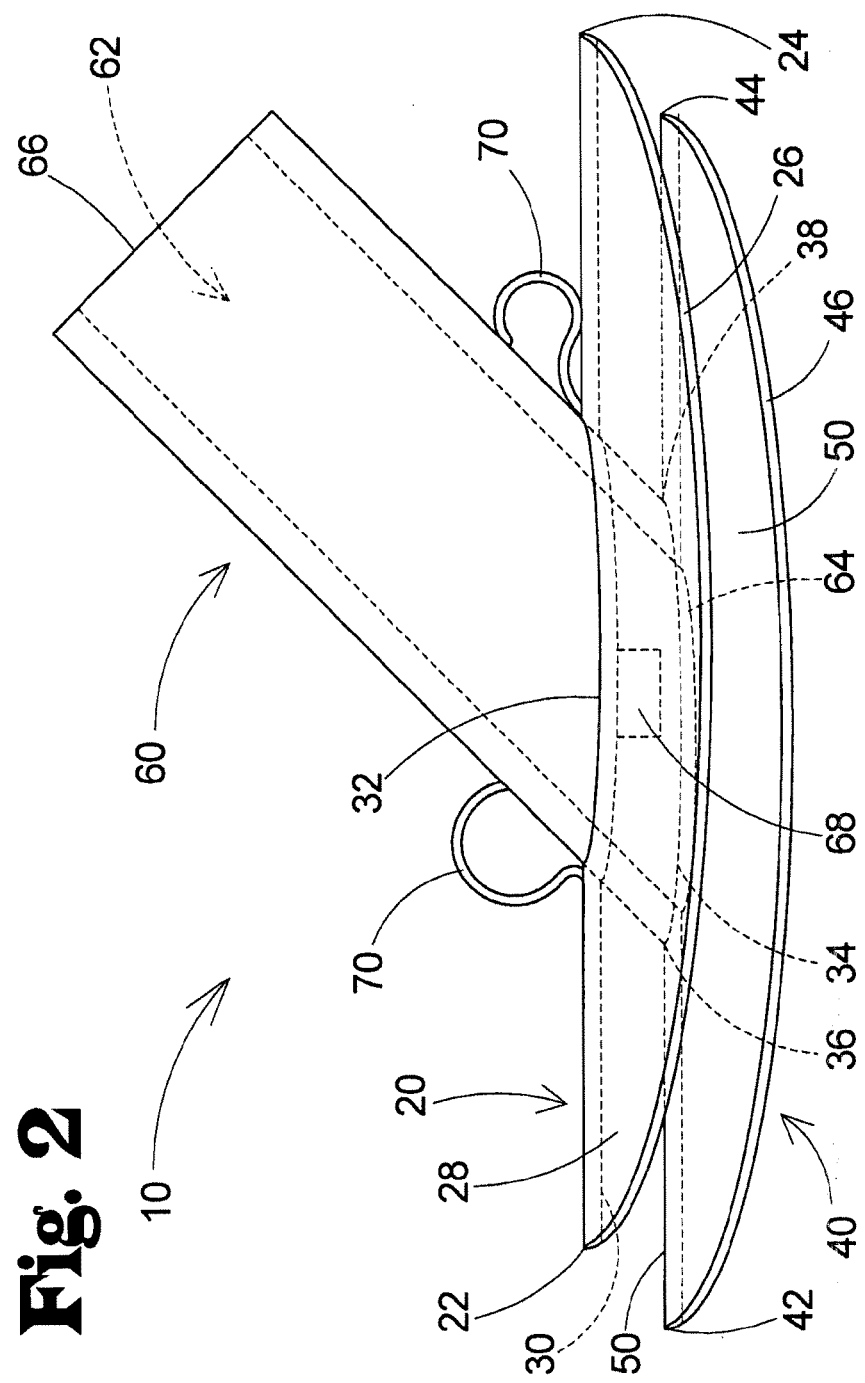
FIG. 2 is a schematic side view of the vascular anastomosis device of FIG. 1.
Figure 5:
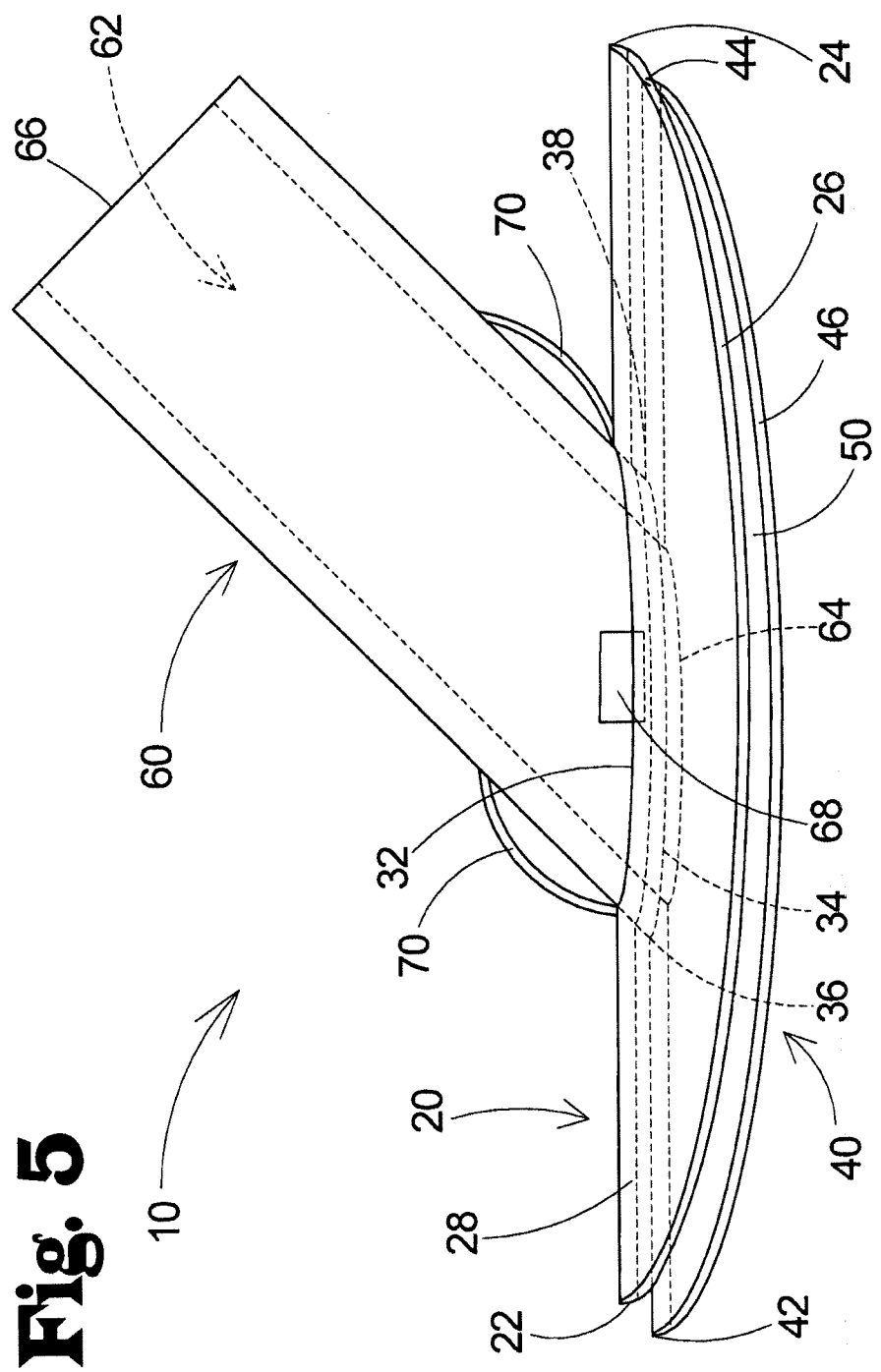
FIG. 5 is a side view of the vascular anastomosis device of FIG. 1 in a closed configuration.

The upper flange (20) is movable from a first, or open, position, which is defined as relatively distant from lower flange (40) such as is illustrated in FIG. 2 to a second, or closed, position, which is defined as relatively proximal to the lower flange (40) such as is illustrated in FIG. 5. When installing the vascular anastomosis device (10) on a first vascular conduit (1), such as is illustratively shown in FIGS. 7 through 13 of the drawings, it may be beneficial to retain the upper flange (20) in the first position as there is room to introduce a portion of vascular tissue (2) of the first vascular conduit (1) between the upper flange (20) and the lower flange (40). Once the vascular anastomosis device (10) is set in its proper place, relative to the insertion incision (80), on the vascular tissue (2) of the first vascular conduit (1), the upper flange (20) may be moved to the second position to grip and seal a portion of the insertion incision (80).

To retain the upper flange (20) in the first position, the vascular anastomosis device (10) may include in some embodiments a retention element (68) that partially inhibits movement of the upper flange (2) from the first position to the second position. The retention element (68) may be integrated into a portion of the vascular anastomosis device (10) or may be separable and removably mounted to the vascular anastomosis device (10). The retention element (68) may hold the upper flange (20) in the first position when attached to the portion of the device (10) and may allow movement of the upper flange (20) when removed from the portion of the device (10). In FIGS. 1 through 6 the retention element (68) is illustratively shown as a pair of block clips mounted on the sides of the diversion conduit (60) that inhibit the upper flange (20) from sliding along the diversion conduit (60) toward the lower flange (40) even under the force of the biasing element (70). By flexing the upper flange (20) along its axis the aperture (32) may be deformed slightly and slightly enlarged to allow the upper flange (20) to slide past the block clips and move to the second position. The block clips may thus be located at a position between the upper flange (20) in the first position and the second position.

FIG. 1 illustrates an embodiment of the vascular anastomosis device (10) with the upper flange (20) in the first position retained by a pair of block clips functioning as the retention element (68). These block clips are shown mounted to the sides of the diversion conduit (60). The biasing element (70) takes the form of a pair of semi-deformable leaves spanning between the anterior and posterior sides of the diversion conduit (60) and the top of the upper flange (20). These leaves are tightly arched due to the relatively high amount of biasing force stored when the upper flange (20) in retained in the first position.

FIG. 2 is a side view of the same embodiment illustrated in FIG. 1. The upper flange (20) is retained in the first position. The outlet (66) of the diversion conduit (60), as well as the outlet end of the diversion conduit (60), may be a simple termination of the tube. It should be understood that a variety of end to end anastomotic structures could be included or integrated into the diversion conduit (60) to accomplish the entire anastomosis procedure, such as; the connector device taught in U.S. Pat. No. 6,036,705, or the anastomotic fitting taught in U.S. Pat. No. 4,368,736, or the projecting barbs of U.S. Pat. No. 5,921,995, but as the specific strategy of end to end connection to the second vascular conduit (not shown) is not included in the scope of the invention no specific apparatus or mechanism is illustrated.

Figure 3:
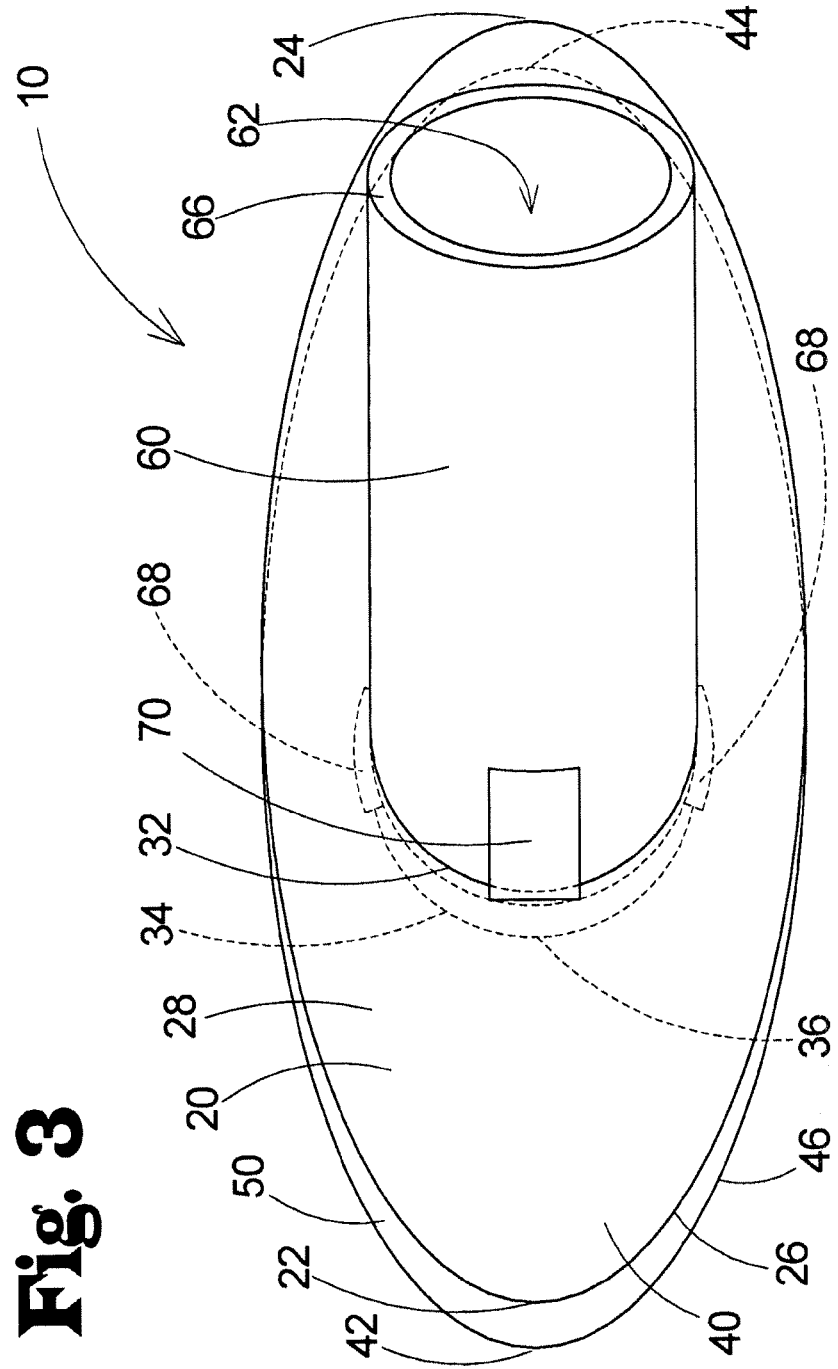
FIG. 3 is a schematic top view of the vascular anastomosis device of FIG. 1.

FIG. 3 is a top view of the same embodiment illustrated in FIG. 1. The perimeter (26) of the upper flange (20) and the perimeter (46) of the lower flange (40) in this embodiment have a generally oval shape, but the invention is not so limited. The shape of the upper and lower flanges (20) and (40) may take a wide variety of shapes in various embodiments to better adapt the vascular anastomosis device (10) to the specific anastomotic situation in which it is to be employed. Such changes to the shape may include elongations to the lower anterior end (42) to help direct the device down along the vascular channel of the first vascular conduit (1), a thinner posterior section of the upper flange (20) and the lower flanges (40) to make the footprint of the clamp formed by the upper (20) and lower (40) flanges as small as possible on the non incision side, or the upper (20) and lower (40) flanges may be curved to conform to a curve that naturally exists in the location of the anastomosis in the first vascular conduit (1).

Figure 4:
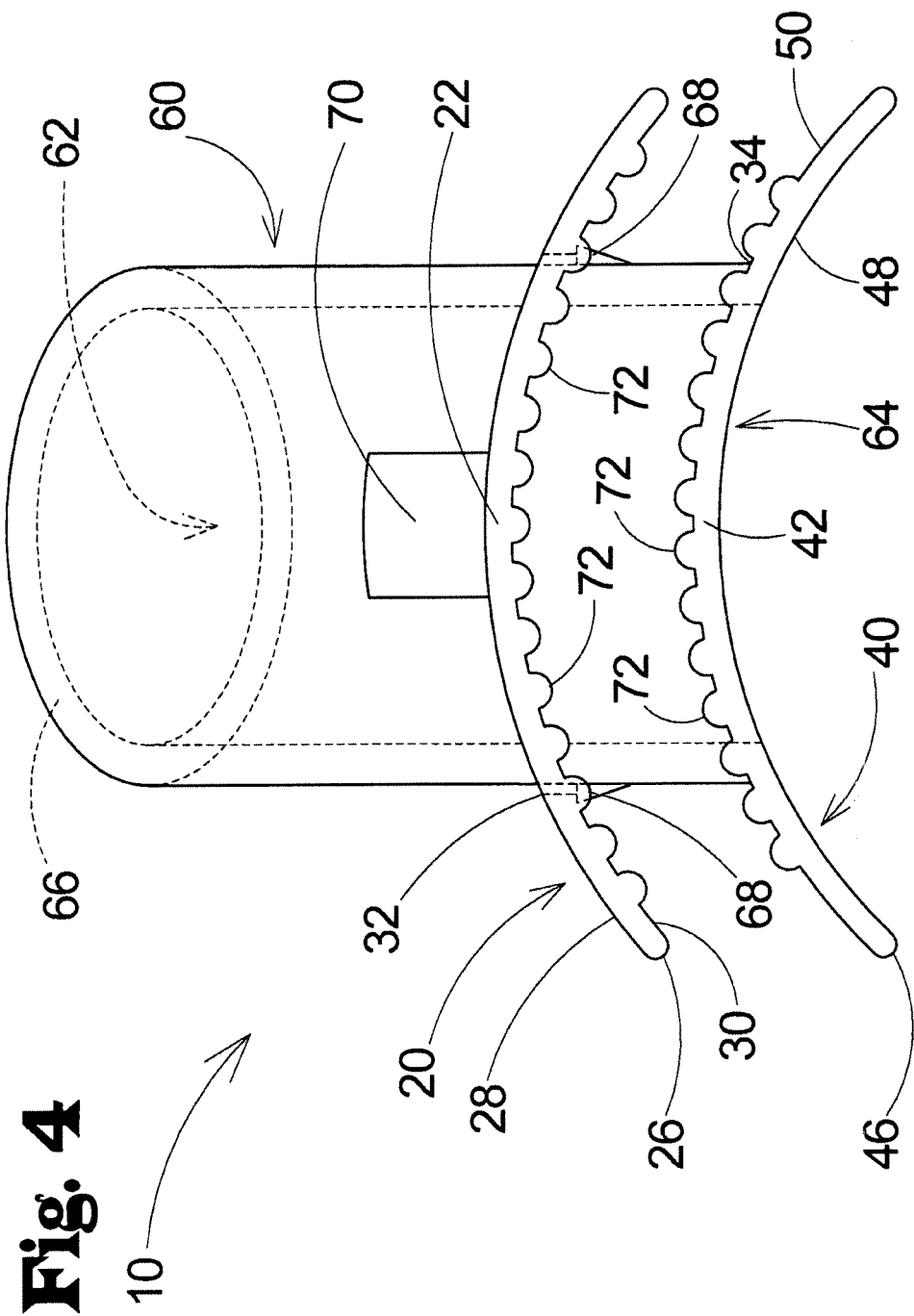
FIG. 4 is a schematic front view of the vascular anastomosis device of FIG. 1.

FIG. 4 is a front view of an embodiment similar to the embodiment illustrated in FIG. 1 with the upper flange (20) located in the first position. In this embodiment a topographic texturing (72) has been added to the upper gripping surface (30) and the lower gripping surface (50). FIG. 4 illustrates a series of rounded protrusions, but different textures or contours could be employed. For example, such texturing may include bumps, raised lines, crosshatching, scaled patterns, wedges, irregular protrusions, tines, spikes and or barbs either in a single pattern or any combination. The texturing on the upper gripping surface (30) as shown in FIG. 4 is reciprocal to the pattern of the lower gripping surface (50) so that the protrusions and gaps between protrusions of the patterns nest with one another, but the relation of the pattern of the upper gripping surface (30) to the pattern of the lower gripping surface (50) may include any complementary or non-complementary relationship.

The embodiment shown in FIG. 5 is similar to the embodiment shown in FIG. 2 but the upper flange (20) is shown in the second, or closed, position. This figure shows that the biasing element (70) is relatively relaxed compared to its condition in the first position shown in FIG. 2, and as a result the tension force exerted by the biasing element (70), while still present, is much diminished compared to FIG. 2. The amount of force exerted by the biasing element (70) in the second position is preferably sufficient to hold the vascular tissue (2) of the first vascular conduit (1) in place and seal against loss of any vascular contents.

Figure 6:
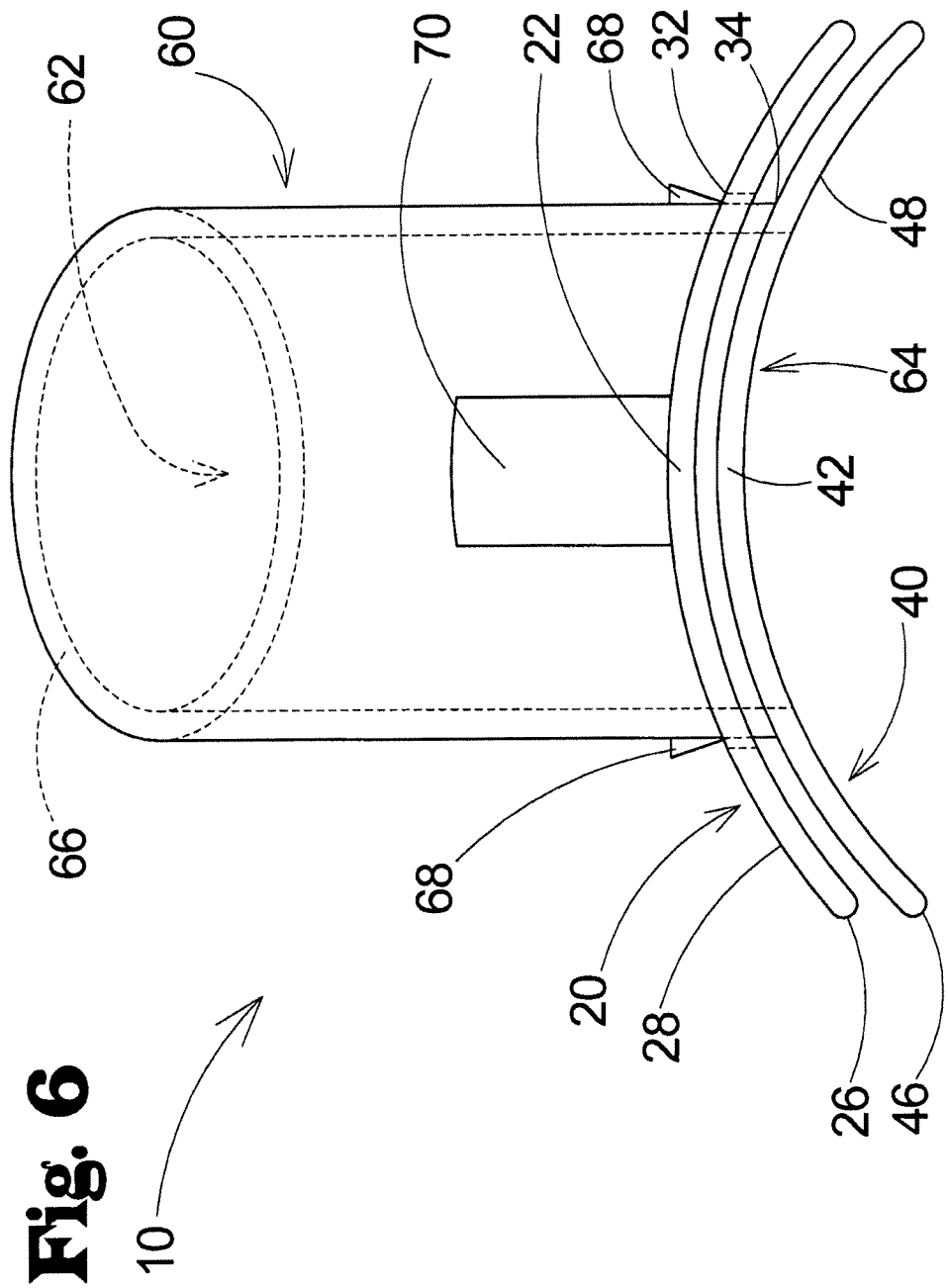
FIG. 6 is a schematic front view of the vascular anastomosis device of FIG. 5.

The embodiment shown in FIG. 6 is similar to the embodiment shown in FIG. 4 with the exceptions that no texturing is present on the upper or lower gripping surfaces (30) and (50) and that the upper flange (20) is shown in the second position. In this embodiment, the arc of the curvature of the upper flange (20) and the lower flange (40) is approximately 90° but the invention is not so limited. The arc of the curvature of the upper (20) and lower (40) flanges at their respective widest extents may be as small as the width of the diversion conduit (60) or large enough to encompass a full 360° arc, or any fraction thereof.

An illustrative implementation of a method for installing the vascular anastomosis device (10) is illustrated in the series of steps illustrated in FIGS. 7 through 13. Alternative methods may be employed depending on such variables as the particular model or design of the vascular anastomosis device (10), the specific environment into which the vascular anastomosis device (10) is to be installed and/or the method of accessing the location of the vascular anastomosis. For example the process may include many changes if the procedure is performed endoscopically as opposed to a simple subcutaneous or inter-muscular procedure. The illustrated process is meant to be exemplary of the general method of installing the vascular anastomosis device (10) although many variations may be apparent to those skilled in the art.

In FIG. 7, a section of the first vascular conduit (1) adequate for the installation of a vascular anastomosis device (10) is selected. A suitable model of vascular anastomosis device (10) is chosen for installation from a plurality of different sizes, shapes and gauges of vascular anastomosis devices (10) that conforms to the surgical requirements and the characteristics of the first (1) and second vascular conduits.

The first vascular conduit (1) may be compressed at the outer limits of the installation area with clamps (3) to suspend the flow of the content of the vessel. The specific model of vascular anastomosis device (10) may dictate the length of the insertion incision (80) in that the overall length of the incision may be equal to the sum of the distance from either the lower anterior end (42) to the anterior side of the seam (36) or the lower posterior end (44) to the posterior end of the seam (38), and half the circumference of the seam (34) of the vascular anastomosis device (10) to be installed. As illustrated in FIG. 7, the section of the insertion incision (80) equal to the distance between the lower posterior end (44) and the perpendicular tangent of the seam (34) will be referred to as incision section A (86). The section of the insertion incision (80) equal to the distance of half the circumference of the seam (34) and will be referred to as incision section B (88). The sum of insertion section A (86) and insertion section B (88), which equals the entire length of the insertion incision (80), will be referred to as incision section C (90). Each model of vascular anastomosis device (10) may include with it a template or measuring device indicating the various incision lengths related to the particular model. This measuring device may be used to either mark the first vascular conduit (1) prior to making the insertion incision (80) or be used during incising as a reference tool.

Next, the insertion incision (80) is made with a scalpel (4) or other incising device in accordance to the defined length indicated for the vascular anastomosis device (10) being utilized. The insertion incision (80) may be defined as having a first end of incision (82) and a second end of incision (84) as reference points for illustrating the installation procedure. After the insertion incision (80) has been made in the first vascular conduit (1) a suture thread (5) may be passed through the vascular tissue (2) with a surgical needle near each side of the insertion incision (80) near or at the junction of incision section A (86) and incision section B (88).

Figure 8:
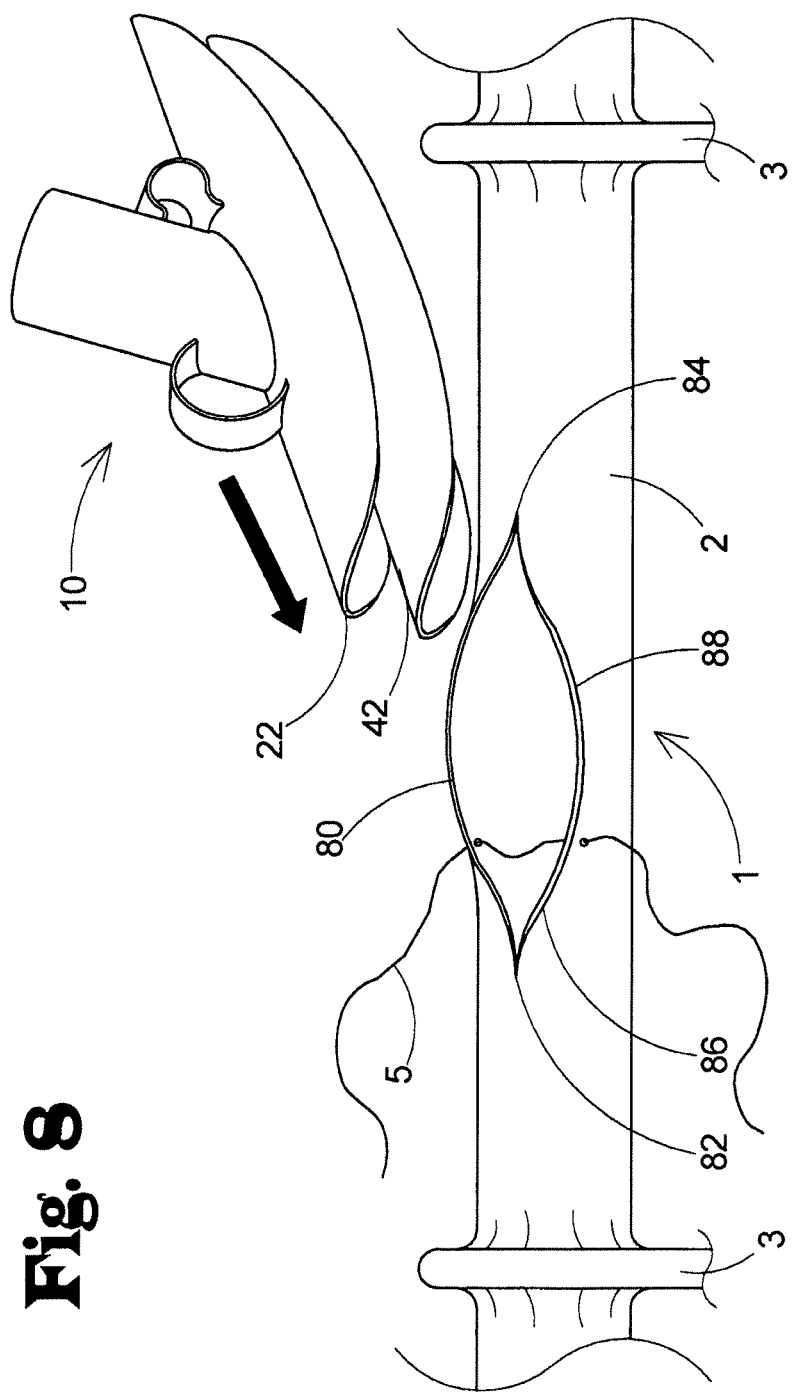
FIG. 8 is a schematic view of a vascular conduit with the incision being opened to accept a vascular anastomosis device.

As illustrated in FIG. 8, the insertion incision (80) may be opened in preparation of receiving the vascular anastomosis device (10). The suture thread (5) spans the open distance between the sides of the insertion incision (80). The upper flange (20) of the vascular anastomosis device (10) is set in the first position so that there is sufficient space between the upper flange (20) and the lower flange (40) to introduce a portion of the vascular tissue (2) of the first vascular conduit (1) between them. The upper flange (20) may be retained in the first position through the agency of the retaining element (68).

Figure 9:
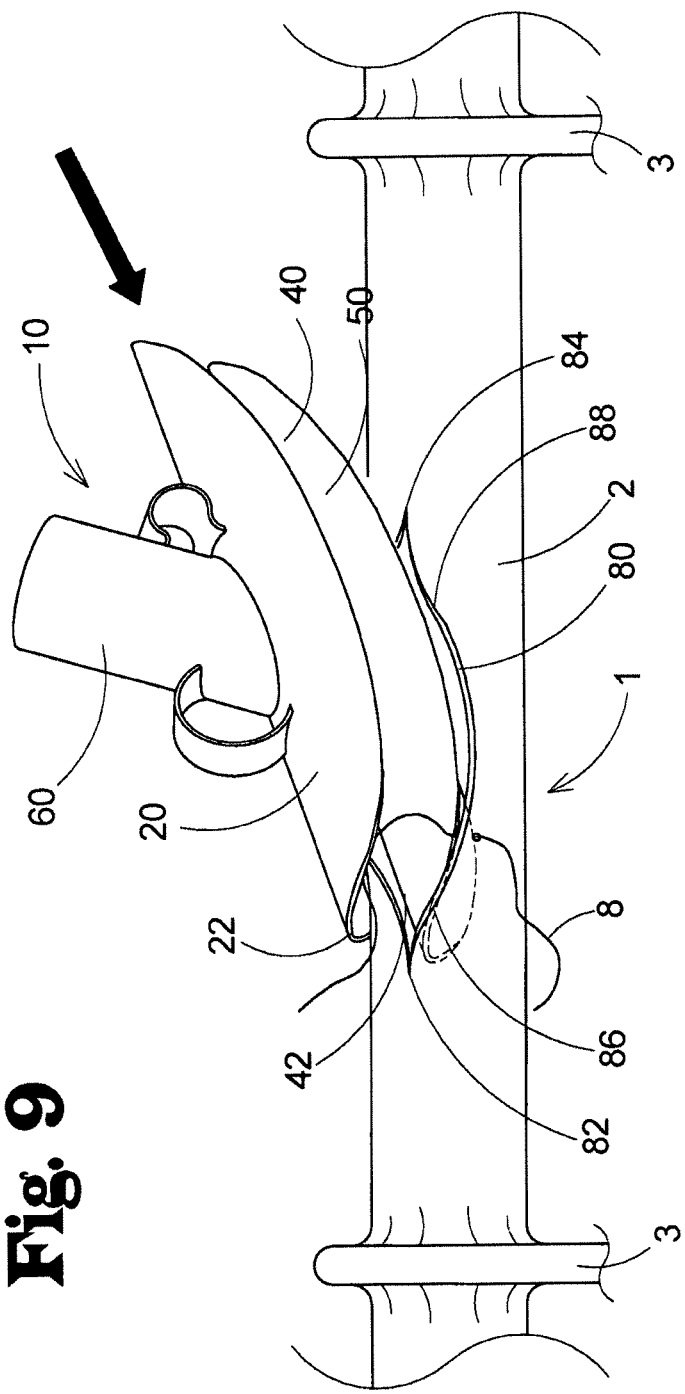
FIG. 9 is a schematic view of a vascular conduit accepting the insertion of the anterior end of a vascular anastomosis device.

FIG. 9 illustrates the integration of the vascular anastomosis device (10) with the first vascular conduit (1). The lower anterior end (42) of the lower flange (40) is inserted into the insertion incision (80) and within the interior of the first vascular conduit (1), while the upper anterior end (22) of the upper flange (20) remains on the exterior of the first vascular conduit (1) thus capturing a portion of the vascular tissue (2) between the upper (20) and lower (40) flanges. While performing the insertion of the vascular anastomosis device (10) into the first vascular conduit (1) the suture thread (5) may also be captured between the upper (20) and lower (40) flanges. Although this step of the procedure requires proper guidance of the vascular anastomosis device (10) into the first vascular conduit (1), the entire process only requires the movement of the vascular anastomosis device (10) toward the first end of the incision (82).

Figure 10:
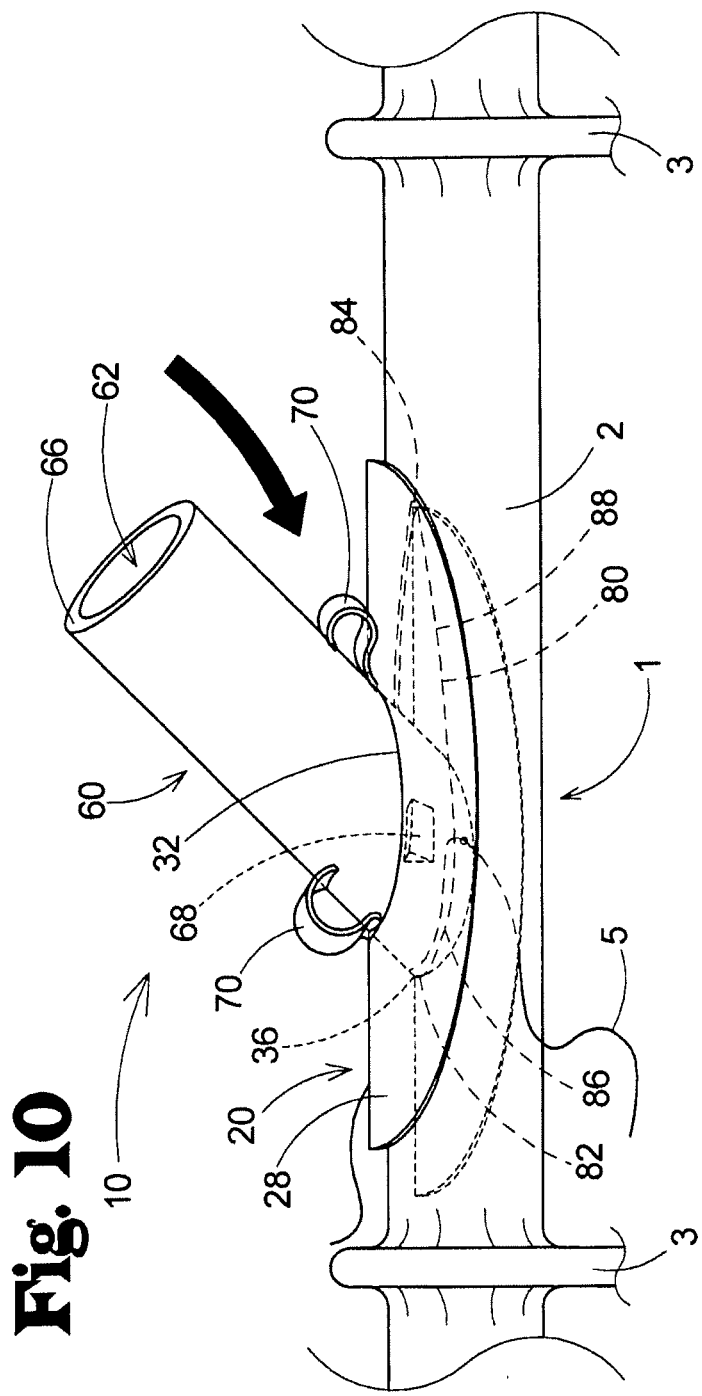
FIG. 10 is a schematic view of a vascular conduit wherein the lower posterior end of a vascular anastomosis device is inserted into the vascular conduit.

In FIG. 10 the upper flange (20) of the vascular anastomosis device (10) is shown still in the first position and the lower flange (40) of the vascular anastomosis device (10) has been moved into the first vascular conduit (1) to the point that the first end of the incision (82) is in contact with the anterior side of the seam (36). With the vascular anastomosis device (10) in this position, the lower posterior end (44) of the lower flange (40) should be relatively close to the second end of the incision (84). At this point the lower posterior end (44) of the lower flange (40) may be inserted into the first vascular conduit (1) so that the entirety of the lower flange (40) is located within the first vascular conduit (1) and the entirety of the upper flange (20) is located outside of the first vascular conduit (1).

Figure 11:
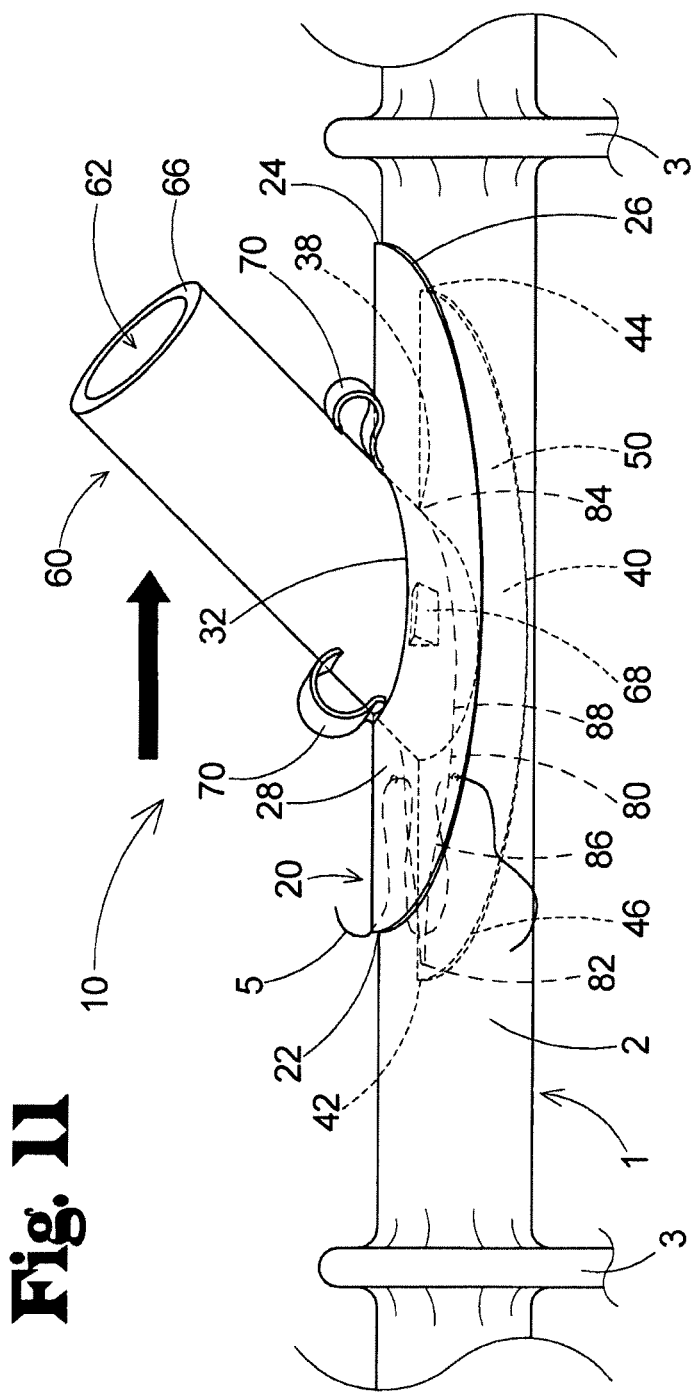
FIG. 11 is a schematic view of a vascular conduit showing the appropriate placement of a vascular anastomosis device within the vascular conduit in accordance with one embodiment of the present invention.

In FIG. 11, the upper flange (20) of the vascular anastomosis device (10) is shown still in the first position. The vascular anastomosis device (10) has been moved along the length of the first vascular conduit (1) to the point at which the second end of the incision (84) is in contact with the posterior side of the seam (38). This placement would locate the seam (38) near or at the junction of incision section A (86) and incision section B (88) where the suture thread (5) has been passed through the vascular tissue (2).

Figure 12:
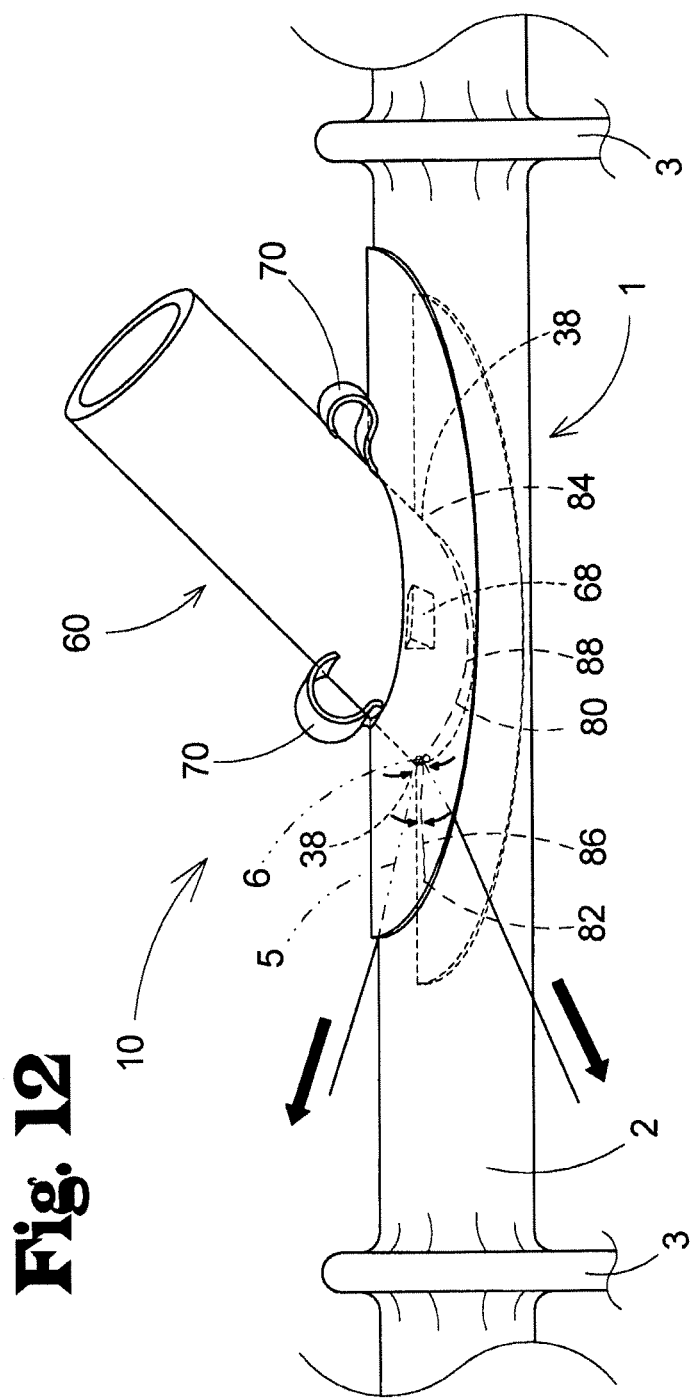
FIG. 12 is a schematic view of a vascular conduit with a knot being tied on the suture to close up a section of the incision.

As is illustrated in FIG. 12, the suture thread (5) may be tightened to eliminate the slack produced by moving the vascular anastomosis device (10) to a point which the anterior side of the seam (36) is in contact with the first end of the incision (82). A simple knot (6) may be tied with the free ends of the suture thread (5) that when tightened will cinch incision section B (88) around the seam (34). The tightening of the knot (6) also tends to bring the sides of incision section A (86) together so that they lie parallel to or in contact with one another.

Figure 13:
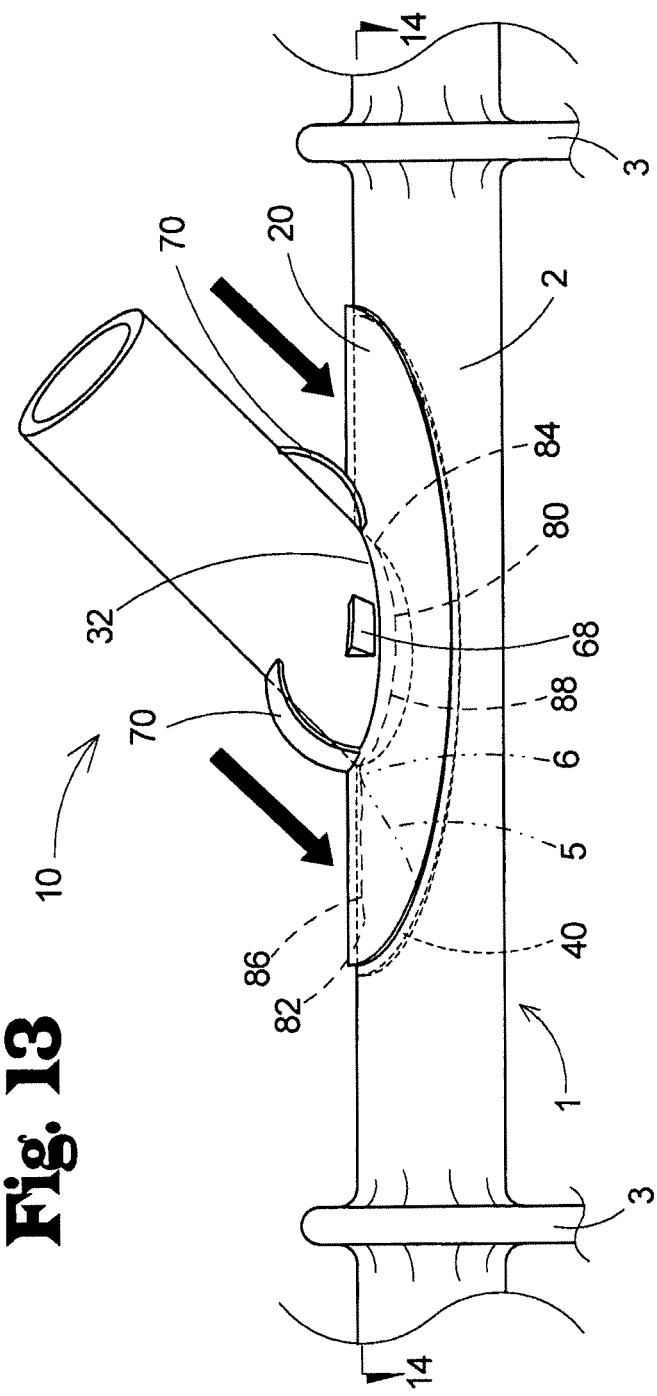
FIG. 13 is a schematic view of a vascular conduit with the vascular anastomosis device being configured to its closed configuration.

FIG. 13 illustrates the movement of the upper flange (20) from the first position to the second position which acts to clamp the vascular tissue (2) of the first vascular conduit (1) between the upper and lower flanges (20) and (40). The area of the upper flange (20) and the lower flange (40) most preferably should encompass and cover the entire insertion incision (80) and should apply a continuous direct pressure provided by the biasing element (70) on the vascular tissue (2). The clamp formed by the upper (20) and lower (40) flanges may form a seal sufficient to resist any loss of the contents of the vessel through the incision. Additional sealing means such as bio-adhesives coated on the upper and lower gripping surfaces (30) and (50) may further insure an adequate seal.

At this point in the procedure the vascular clamps (3) may be released to restore the flow of fluid through the first vascular conduit (1), provided the outlet (66) of the diversion conduit (60) has been capped, plugged or otherwise blocked from discharging the contents of the first vascular conduit (1). This restoration of flow while the other end of the anastomosis is worked on benefits the health of the proximate tissue and the health of the patient in general. When the other end of the anastomosis is prepared for connection to the outlet (66) of the diversion conduit (60), the vascular clamps (3) may be reapplied for only the amount of time required to complete the seal of the diversion juncture thus reducing the duration of suspended flow significantly in comparison to the currently practiced method.

Figure 14:
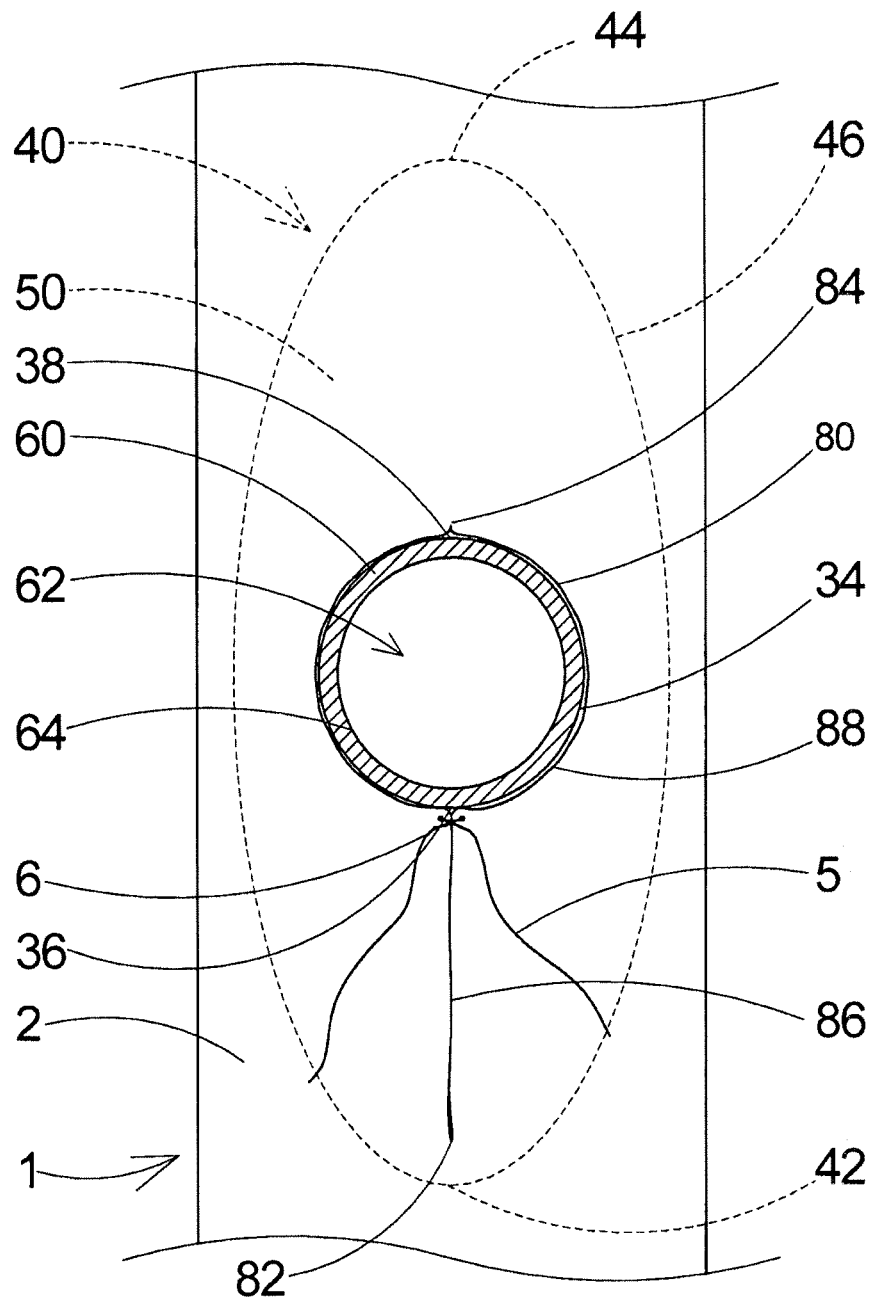
FIG. 14 is a schematic cross-sectional view of the vascular anastomosis device of FIG. 13 showing the arrangement of the incision, knot and suture.

FIG. 14 illustrates a top view of the arrangement of the insertion incision (80), both sections A (86) and B (88), the placement of the suture thread (5) and knot (6), and the relation of the upper and lower flanges (20) and (40) position as demonstrated in FIG. 13.

Figure 15:
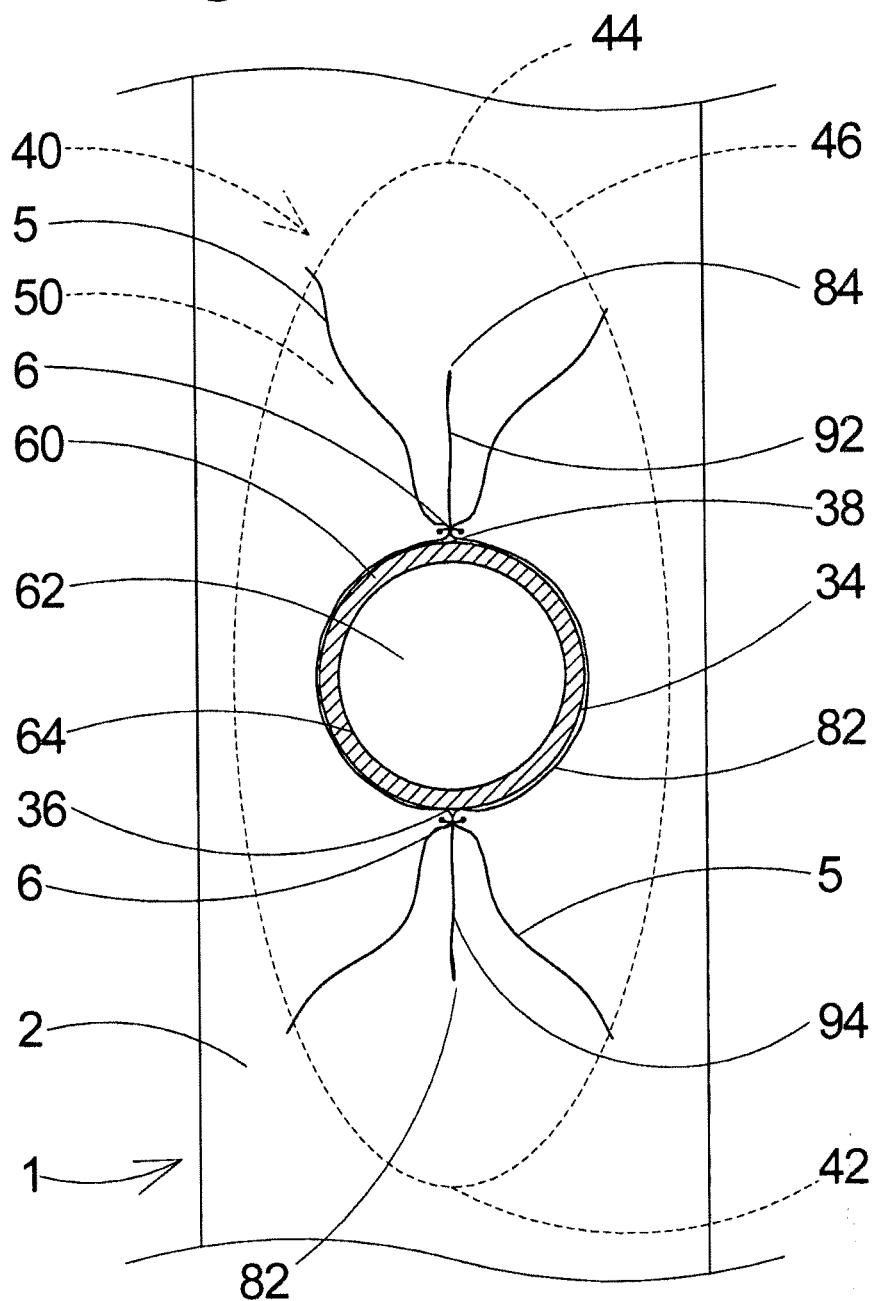
FIG. 15 is a schematic cross-sectional view of the vascular anastomosis device demonstrating an alternative, two suture embodiment of the present invention.

FIG. 15 illustrates an optional implementation different from that depicted in FIG. 14, wherein the placement of a pair of suture threads (5) positions the vascular anastomosis device (10) in a more central location within the insertion incision (80). In this embodiment the length of incision section A (86) may be divided into two portions hereafter referred to as incision section D (92) and incision section E (94). One benefit of this arrangement is that the distance between the first (82) and second (84) ends of the incision and the upper (26) and lower (46) perimeters of the upper (20) and lower (40) flanges respectively is greater, and thus the implementation may be less likely to leak. The time expended by including an additional suture thread (5) and knot (6) and the time taken to assure proper placement of the suture thread (5) between the upper (24) and lower (44) posterior ends of the upper (20) and lower (40) flanges is typically not significant in comparison to the benefit, and is still may be considerably faster that the currently practiced method. To practice this method, the measuring template accompanying the particular vascular anastomosis device (10) may include measurements of incision section D (92) followed by incision section B (88) and finally incision section E (94) to indicate the length of the incision section A (86) and the placement of the suture threads (5) at the junction of incision section D (92) and incision section B (88) and the junction of incision section B (88) and incision section E (94).

Figure 16:
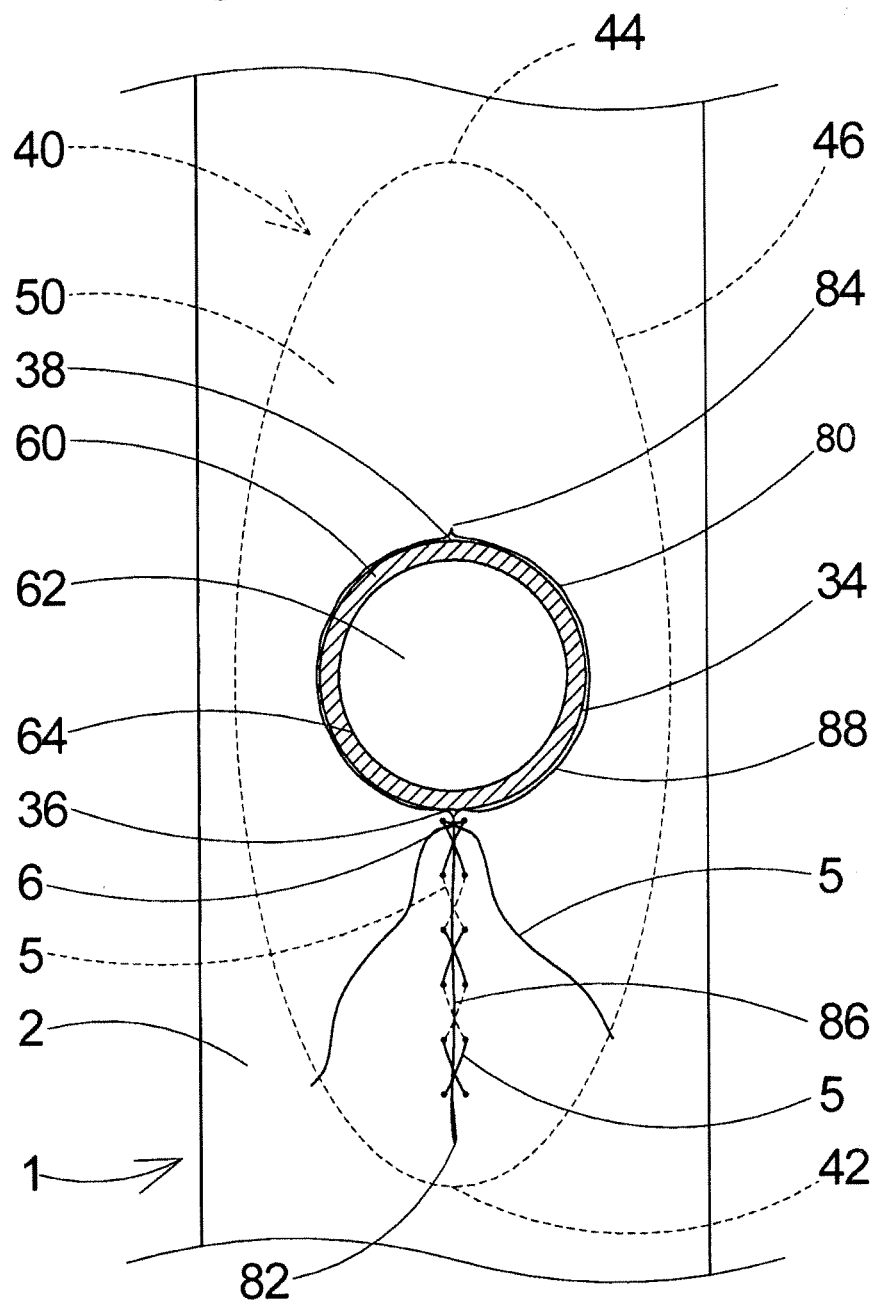
FIG. 16 is a schematic cross sectional view of a vascular anastomosis device demonstrating a bootlace suture embodiment of the present invention.

FIG. 16 illustrates another optional implementation of the method of arranging the suture thread (5). In this embodiment the suture thread (5) has been configured in a crossed arrangement producing a boot lace pattern along the length of incision section A (86) to facilitate a more dependable closure between the two sides of incision section A (86). Many other suturing strategies, such as ladder lacing or loop stitching, will be evident to those skilled in the art. Such optional suturing patterns may be applied to the optional placement methods, such as the placement method depicted in FIG. 15.

Figure 17:
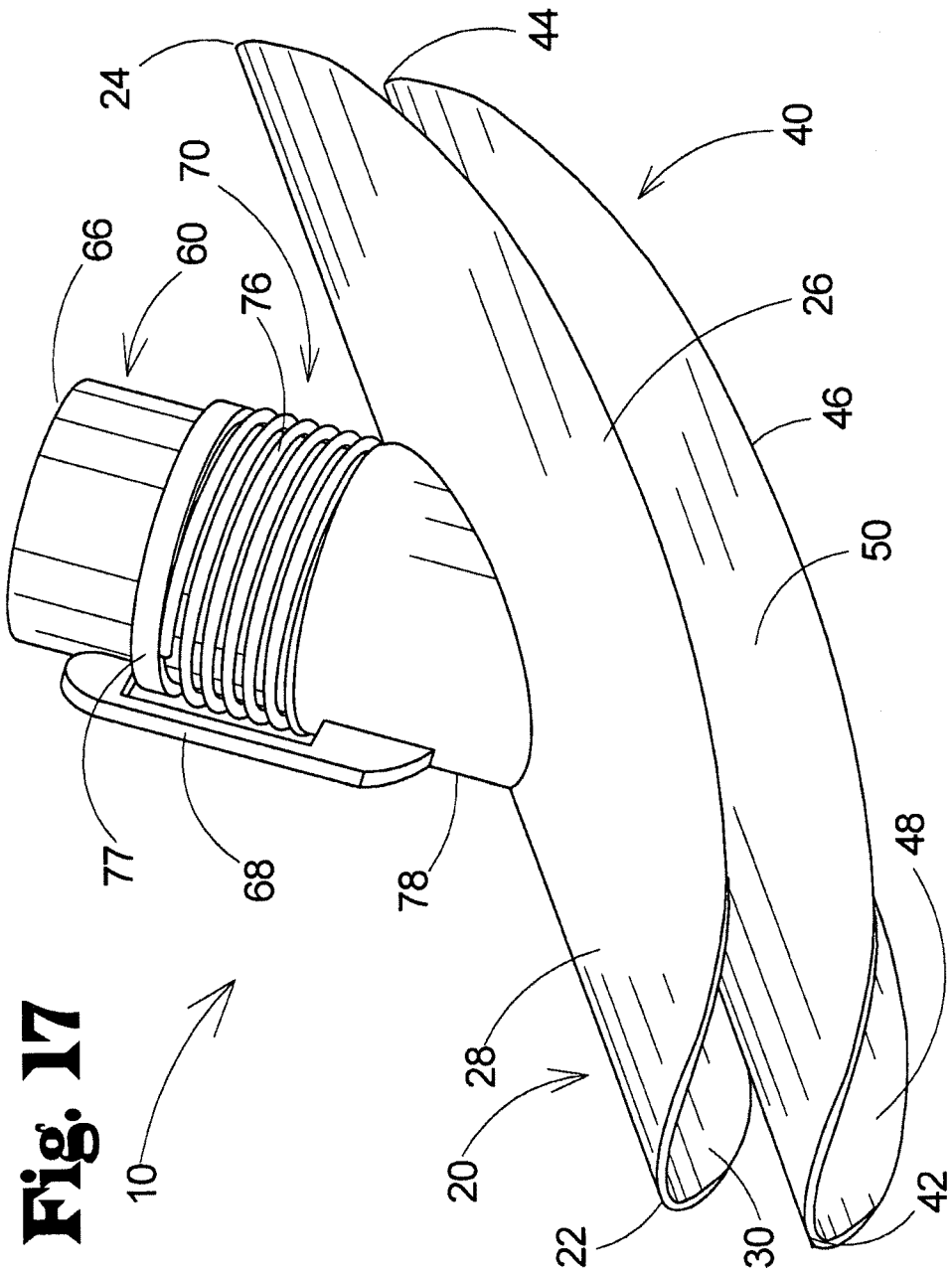
FIG. 17 is a schematic perspective view of a vascular anastomosis device demonstrating a coil spring biasing element in accordance with another embodiment of the present invention.

In FIG. 17, an embodiment of the vascular anastomosis device (10) is shown with the upper flange (20) in the first position. The biasing device (70) in this embodiment comprises a compression spring (76), The compression spring (76) is shown compressed between a raised ring (77) mounted on the upper section of the exterior of the diversion conduit (60) and a collar (78) encompassing the lower section of the of the diversion conduit (60) and integrated to the upper flange (20). In this particular embodiment the retention element (68) comprises a latching hook clip extending from the collar (78) and hooking above the ring (77). When the hook clip is released from the ring (77) or removed entirely, the compression spring (76) pushes the collar (78) down along the length of the diversion conduit (60) thus bringing together the upper gripping surface (30) and the lower gripping surface (50) in a vise like manner.

Figure 18:
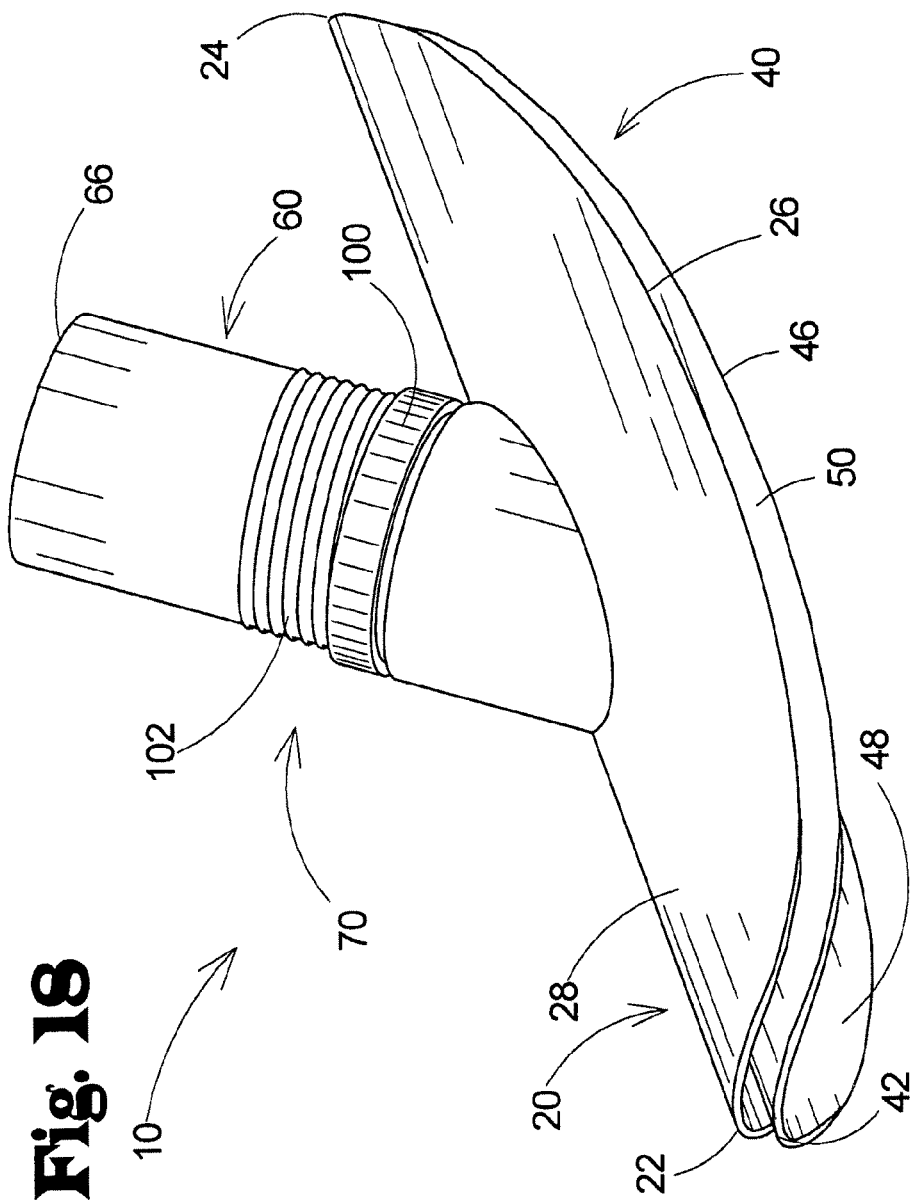
FIG. 18 is a schematic perspective view of a vascular anastomosis device demonstrating a threaded screw biasing element in accordance with yet another embodiment of the present invention.

In FIG. 18, an embodiment of the vascular anastomosis device (10) is shown with the upper flange (20) in the second position. The biasing element (70) in this embodiment comprises a ring (100) with a threaded interior that engages complementary threads (102) which are part of the diversion conduit (60). By twisting the ring (100), pressure is exerted on the collar attached to the upper flange (20) and encompassing the lower section of the diversion conduit (60) causing the upper gripping surface (30) and the lower gripping surface (50) to come together. As the threaded screw mechanism is a passive biasing mechanism, and requires the anastomosis performer to twist the ring (100) to provide a biasing force, there is no need for a retention element (68) to keep the upper flange (20) in the first position.

Figure 19:
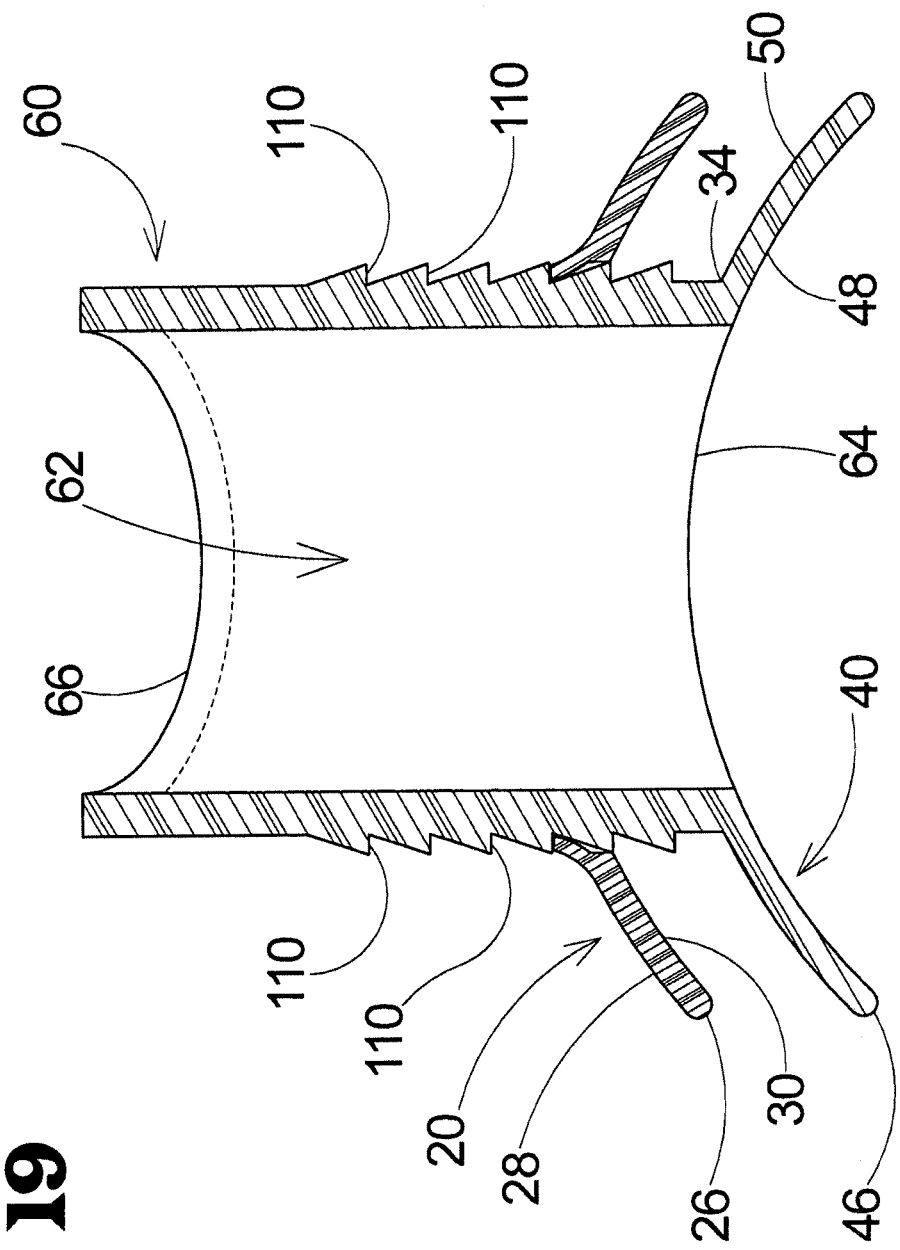
FIG. 19 is a cross-sectional view of a vascular anastomosis device demonstrating a linear ratchet biasing device in accordance with another embodiment of the present invention.

Illustrated in FIG. 19 is an embodiment of the vascular anastomosis device (10) with the upper flange (20) in transition position between the first position and the second position. The biasing element (70) in this embodiment comprises a linear series of teeth or barbs or cogs (110) mounted to the diversion conduit (60) that are engaged by flexible locking blocks (112) mounted to the sides of the upper flange (20). As the upper flange (20) descends along the length of the exterior of the diversion conduit (60), the blocks flex to allow the passage of each cog in one direction but are biased against allowing movement in the opposite direction. This embodiment of the biasing element (70) comprises a passive biasing mechanism as it requires the anastomosis performer to move the upper flange (20) from the first position to a second position while the biasing mechanism sustains the force. It is anticipated that the biasing element (70) illustrated here may be used in combination with other biasing elements (70) that would provide force to the upper flange (20) such as; the compression spring of FIG. 18 or the leaf springs of FIGS. 1 through 6, to provide the clamping force required to assure the integrity of the seal.

FIG. 20 illustrates an embodiment of the vascular anastomosis device (10) that includes a removable retention element (68). The retention element (68) in this embodiment comprises a clip (120) with a hook on both ends and a pair of detents, one (122) integrated into the diversion conduit (60) and the other (124) integrated into the upper flange (20), that are designed to engage the hook ends of the clip (120). The clips (120), when the hooks (122) on both ends are engaged with both the detents (124) would serve to retain the upper flange (20) in the first position. When the one of the hooks is disengaged on both clips the upper flange (20) is released to so that it may move to the second position either under the influence of the biasing force of an active biasing element (70) or through the agency of the anastomosis performer. If the hooks on both ends of the clips are disengaged the clip may be removed from the vascular anastomosis device (10).

FIG. 21 depicts an embodiment of the vascular anastomosis device (10) with an upper flange (20) that extends only to the anterior side of the diversion conduit (60). The dashed line indication for the upper flange (20) is located in the first position while the solid line indication is located in the second position. In this embodiment the biasing element (70) comprises a coil spring (130) that is mounted on a hinge mechanism (132) that is fixed to the side of the diversion conduit (60). This hinge also connects the upper flange (20) to the diversion conduit (60). It is anticipated that an additional biasing element (70) may include a locking hinge mechanism integrated within the hinge. The retention device (68) in this embodiment may take the form of a wedge shaped clip (134) mounted to the anterior side of the diversion conduit (60). The clip may retain a portion of the posterior edge of the upper flange (20) that conforms to the anterior side of the seam (36) when in the second position. This embodiment also includes a shorter and narrower lower posterior end (44) to reduce the length of the insertion incision (80) so that the smaller upper flange (20) and lower flange (40) clamping footprint is still sufficient to fully seal incision section A (86) when in the second position. Although the structure of this embodiment differs in some aspects from the embodiment illustrated in FIGS. 1 through 6 it still conforms to the definition of a vascular anastomosis device (10) as set forth in these specifications.

When employing a vascular anastomosis device (10) such as is illustrated in FIG. 21, the method of installation may take advantage of a sutureless approach. The first position of the upper flange (20) in this embodiment is sufficiently open enough to allow the anastomosis performer to place the edges of incision section A (86) in contact with one another. This placement may be sustained through the agency of texturing or contouring on the lower gripping surface (50) and/or through the use of bio-adhesives included on the lower gripping surface (50) as described above. The upper flange (20) may then be moved to the second position without the need for a suture thread (5) or knot (6) to hold incision section A (86) together before applying the clamping force.

As illustrated in FIG. 22, in another embodiment, the upper flange (20) of the vascular anastomosis device (10) includes a plurality of perforations (74). These perforations (74) allow vascular tissue (2) of the second vascular conduit (not shown) to be in contact with the vascular tissue (2) of the first vascular conduit (1). The contact between the first vascular conduit (1) and second vascular conduit (not shown) may promote the growth of tissue between the conduits which may be necessary if the vascular anastomosis device (10) is designed to dissolve and be absorbed by the patient's body. Such bio-dissolvable or bio-absorbable materials are well known to those skilled in the art and the specific material would be chosen based on the amount of time expected for the first vascular conduit (1) and the second vascular conduit (not shown) to mend sufficiently to provide a reliable seal. The size, shape and distance between the perforations (74) may be dependent on the specific strategies involved in the particular anastomosis procedure and may vary from a single perforation (74) to a plurality of perforations (74) such that the structure may be characterized as a mesh. Still further, the various other embodiments of the device (10) shown in the Figures are each amenable to use of perforations such as perforations (74).

When employing a vascular anastomosis device (10) designed to be absorbed into the patient's body, the procedure for attaching the second vascular conduit may include expanding the end of the second vascular conduit or providing additional vascular tissue (2) of the second vascular conduit to overlay the perforations (74) of the upper flange (20) so that sufficient growth between the first vascular conduit (1) and second vascular conduit can provide a natural vascular seal prior to the bio-dissolution of the upper and lower flanges (20) and (40) which provide the prosthetic vascular seal.

It should be appreciated from the foregoing description that, except when mutually exclusive, the features of the various embodiments described herein may be combined with features of other embodiments as desired while remaining within the intended scope of the disclosure.

Thus, the invention may provide a mechanism that includes a spring biased flange which when used in conjunction with a second compatibly shaped flange seals the insertion incision between the two flanges with as few as a single suture.

The vascular anastomosis device of the invention may become a permanent stent within the body of the patient assuring many years of unobstructed flow. The anastomosis device may include structural and compositional characteristics that allow the sections of vascular tissue to mend together while the device itself dissolves and is absorbed into the patient's body.

It should be appreciated from the foregoing description and the many variations and options disclosed that, except when mutually exclusive, the features of the various embodiments described herein may be combined with features of other embodiments as desired while remaining within the intended scope of the disclosure.

It is to be understood that the above description is intended to be illustrative, and not restrictive. Many other embodiments and combinations of elements will be apparent to those skilled in the art upon reviewing the above description and accompanying drawings. The scope of the invention should, therefore, be determined with reference to the appended claims, along with the full scope of equivalents to which such claims are entitled.

What is claimed is:

1. A method of installing a vascular anastomosis device, the method comprising:
    clamping off flow through a portion of a vascular conduit, using two clamps at opposite ends of the portion of the vascular conduit;
    creating an incision in vascular tissue of the vascular conduit for insertion of the vascular anastomosis device;
    passing a suture thread through the vascular tissue of the vascular conduit near each of two sides of the incision at a location that is closer to a first end of the incision than to a second end of the incision;
    opening the incision, in preparation for receiving the vascular anastomosis device;
    maintaining an upper flange of the vascular anastomosis device in a first position, using a retention member on a diversion conduit of the vascular anastomosis device, so that there is sufficient space between the upper flange and a lower flange of the vascular anastomosis device to introduce a portion of the vascular tissue between the upper flange and the lower flange, wherein the diversion conduit is attached to the lower flange and is configured to pass movably through an aperture in the upper flange;
    inserting a lower anterior end of the lower flange of the vascular anastomosis device through the incision and into the vascular conduit, in a direction toward the first end of the incision, while the upper flange remains on an exterior surface of the vascular conduit, to capture a portion of the vascular tissue and the suture thread between the upper flange and the lower flange;
    advancing the lower anterior end of the lower flange farther toward the first end of the incision to contact an anterior side of a seam between the lower flange and the diversion conduit of the vascular anastomosis device with the first end of the incision;
    inserting a lower posterior end of the lower flange through the second end of the incision into the vascular conduit;
    tightening the suture thread to cinch the incision around the seam;
    moving the upper flange from the first position to a second position, using a biasing member coupled with opposing sides of the upper flange and the diversion conduit, to clamp the vascular tissue of the vascular conduit between the upper flange and the lower flange such that the upper flange and the lower flange cover all of the incision; and
    releasing the two clamps from the vascular conduit to allow blood to flow through the vascular conduit, wherein the diversion conduit has been blocked before releasing the two clamps, to prevent the blood from flowing through the diversion conduit.

2. The method of claim 1, wherein the retention member comprises two clips.

3. The method of claim 1, further comprising tying a knot in the suture thread to hold the sides of the incision in place.

4. The method of claim 1, further comprising holding portions of the vascular conduit at the sides of the incision in place using texturing on a surface of the vascular anastomosis device.

5. The method of claim 1, further comprising holding portions of the vascular conduit at the sides of the incision in place using a bio-adhesive applied on a surface of the vascular anastomosis device.

6. The method of claim 1, further comprising measuring a length for creating the incision.

7. The method of claim 6, further comprising marking the measured length of the incision on the exterior surface of the vascular conduit, before creating the incision.

8. The method of claim 1, further comprising:
    situating the vascular anastomosis device substantially centrally in the incision; and
    suturing the incision on sides of the vascular anastomosis device to close the incision.

9. The method of claim 1, further comprising:
    situating the vascular anastomosis device at one of the first end or the second end of the incision; and
    suturing the incision on a side of the vascular anastomosis device to close the incision.

10. The method of claim 1, further comprising adhering one of the upper and lower flanges to the vascular conduit.

11. The method of claim 1, wherein the biasing element comprises a pair of deformable leaf springs mounted on the opposing sides of the diversion conduit and connecting to an exterior surface of the upper flange.

12. The method of claim 11, wherein one of the deformable leaf springs is attached to an anterior side of the diversion conduit, and wherein the other one of the deformable leaf springs is attached to a posterior side of the diversion conduit.

13. The method of claim 11, wherein one of the deformable leaf springs has an arched shape and the other one of the deformable leaf springs has a different.

* * * * *